(12) United States Patent
Burton et al.

(10) Patent No.: US 6,488,892 B1
(45) Date of Patent: Dec. 3, 2002

(54) SAMPLE-HOLDING DEVICES AND SYSTEMS

(75) Inventors: William G. Burton, Pleasanton, CA (US); Douglas N Modlin, Palo Alto, CA (US); Derrick A. Richardson, Mountain View, CA (US); Jon F. Petersen, Redwood City, CA (US); Joseph S. Leytes, Mountain View, CA (US); John C. Owicki, Palo Alto, CA (US); Amer El-Hage, Menlo Park, CA (US); Lev J. Leytes, Palo Alto, CA (US)

(73) Assignee: LJL BioSystems, Inc., Sunnyvale, CA (US)

( * ) Notice: Subject to any disclaimer, the term of this patent is extended or adjusted under 35 U.S.C. 154(b) by 0 days.

(21) Appl. No.: 09/478,819

(22) Filed: Jan. 5, 2000

Related U.S. Application Data

(63) Continuation of application No. PCT/US99/08410, filed on Apr. 16, 1999, and a continuation of application No. 09/062,472, filed on Apr. 17, 1998, now Pat. No. 6,071,748, which is a continuation of application No. 09/156,318, filed on Sep. 18, 1998, now Pat. No. 6,258,326, which is a continuation of application No. 09/160,533, filed on Sep. 24, 1998, now Pat. No. 6,097,025.

(60) Provisional application No. 60/119,829, filed on Feb. 12, 1999, provisional application No. 60/114,209, filed on Dec. 29, 1998, provisional application No. 60/089,848, filed on Jun. 19, 1998, and provisional application No. 60/085,500, filed on May 14, 1998.

(51) Int. Cl.[7] .............................................. G01N 21/29
(52) U.S. Cl. .................... 422/82.05; 422/63; 422/82.08; 422/99; 422/102; 422/104; 436/43; 436/164; 436/165; 436/172; 356/244; 356/246
(58) Field of Search .......................... 422/52, 63, 82.05, 422/82.08, 99, 101, 102, 104; 436/43, 164, 165, 172; 356/244, 246

(56) References Cited

U.S. PATENT DOCUMENTS

| 3,013,467 A | 12/1961 | Minsky |
| 3,540,858 A | 11/1970 | Rochte et al. |
| 3,849,654 A | 11/1974 | Malvin |
| 4,011,451 A | 3/1977 | Nelson |
| 4,067,653 A | 1/1978 | Fletcher et al. |
| 4,240,751 A | * 12/1980 | Linnecke et al. ........... 356/409 |
| 4,245,052 A | 1/1981 | Lund |
| 4,292,273 A | 9/1981 | Butz et al. |
| 4,501,970 A | 2/1985 | Nelson |

(List continued on next page.)

FOREIGN PATENT DOCUMENTS

| EP | 0 266 881 A2 | 5/1988 |
| EP | 0 542 422 A1 | 5/1993 |
| WO | WO94/29024 | 12/1994 |

OTHER PUBLICATIONS

*Fundamentals of Light Microscopy*, Spencer, Cambridge University Press, 1982.

*Basic Fluorescence Microscopy*, Taylor et al., Methods in Cell Biology, vol. 29, pp. 207–237, 1989.

*Three–Dimensional Confocal Fluorescence Microscopy*, Brakenhoff et al., Methods in Cell Biology, vol. 30, pp. 379–389, 1989.

*Laser Scanning Confocal Microscopy of Living Cells*, Lemasters et al., Optical Microscopy: Emerging Methods and Applications, pp. 339–345, 1993.

Primary Examiner—Jill Warden
Assistant Examiner—Dwayne K Handy
(74) Attorney, Agent, or Firm—Kolisch Hartwell PC

(57) ABSTRACT

Sample-holding devices and systems for efficiently utilizing relatively small-volume fluid samples.

83 Claims, 17 Drawing Sheets

U.S. PATENT DOCUMENTS

| | | |
|---|---|---|
| 4,545,958 A | 10/1985 | Dopatka |
| 4,622,208 A | 11/1986 | Namba et al. |
| 4,626,684 A | 12/1986 | Landa |
| 4,704,255 A | 11/1987 | Jolley |
| 4,707,067 A | 11/1987 | Haberland et al. |
| 4,730,921 A | 3/1988 | Klein et al. |
| 4,735,778 A | 4/1988 | Maruyama et al. |
| 4,741,619 A | 5/1988 | Humphries et al. |
| 4,762,420 A | 8/1988 | Bowley |
| 4,772,453 A | 9/1988 | Lisenbee |
| 4,810,096 A | 3/1989 | Russell et al. |
| D303,149 S | 8/1989 | Andersen |
| 4,868,103 A | 9/1989 | Stavrianopoulos et al. |
| 4,873,633 A | 10/1989 | Mezei et al. |
| 4,892,409 A | 1/1990 | Smith |
| 4,936,682 A | 6/1990 | Hoyt |
| 4,948,442 A | 8/1990 | Manns |
| 4,968,148 A | 11/1990 | Chow et al. |
| 4,979,821 A | 12/1990 | Schutt et al. |
| 5,047,215 A | 9/1991 | Manns |
| 5,084,246 A | 1/1992 | Lyman et al. |
| 5,091,652 A | 2/1992 | Mathies et al. |
| 5,169,601 A | 12/1992 | Ohta et al. |
| 5,206,568 A | 4/1993 | Björnson et al. |
| 5,208,161 A | 5/1993 | Saunders et al. |
| 5,225,164 A | 7/1993 | Astle |
| 5,262,128 A | 11/1993 | Leighton et al. |
| 5,275,951 A | 1/1994 | Chow et al. |
| 5,319,436 A | 6/1994 | Manns et al. |
| 5,340,747 A | 8/1994 | Eden |
| 5,355,215 A | 10/1994 | Schroeder et al. |
| 5,384,093 A | 1/1995 | Ootani et al. |
| 5,401,465 A | 3/1995 | Smethers et al. |
| 5,436,718 A | 7/1995 | Fernandes et al. |
| 5,449,921 A | 9/1995 | Baba |
| 5,457,527 A | 10/1995 | Manns et al. |
| 5,459,300 A | 10/1995 | Kasman |
| 5,487,872 A | 1/1996 | Hafeman et al. |
| 5,512,492 A | 4/1996 | Herron et al. |
| 5,531,697 A | 7/1996 | Olsen et al. |
| 5,531,698 A | 7/1996 | Olsen |
| 5,540,889 A | 7/1996 | Gordon et al. |
| 5,542,012 A | 7/1996 | Fernandes et al. |
| 5,560,811 A | 10/1996 | Briggs et al. |
| 5,589,350 A | 12/1996 | Bochner |
| 5,589,351 A | 12/1996 | Harootunian |
| 5,592,289 A | 1/1997 | Norris |
| 5,604,130 A | 2/1997 | Warner et al. |
| 5,609,828 A * | 3/1997 | O'Bear et al. .............. 422/102 |
| 5,633,724 A | 5/1997 | King et al. |
| 5,650,125 A | 7/1997 | Bosanquet |
| 5,679,310 A | 10/1997 | Manns |
| 5,736,410 A | 4/1998 | Zarling et al. |
| 5,756,050 A | 5/1998 | Ershow et al. |
| 5,770,151 A | 6/1998 | Roach et al. |
| 5,772,966 A | 6/1998 | Maracas et al. |
| 5,780,857 A | 7/1998 | Harju et al. |
| 5,840,256 A | 11/1998 | Demers et al. |
| 5,879,632 A | 3/1999 | Demers |
| 5,882,597 A | 3/1999 | Astle |
| 5,882,930 A | 3/1999 | Baier |
| 5,910,287 A | 6/1999 | Cassin et al. |
| 5,958,694 A * | 9/1999 | Nikiforov ..................... 435/6 |
| 6,027,695 A * | 2/2000 | Oldenburg et al. ......... 422/102 |

* cited by examiner

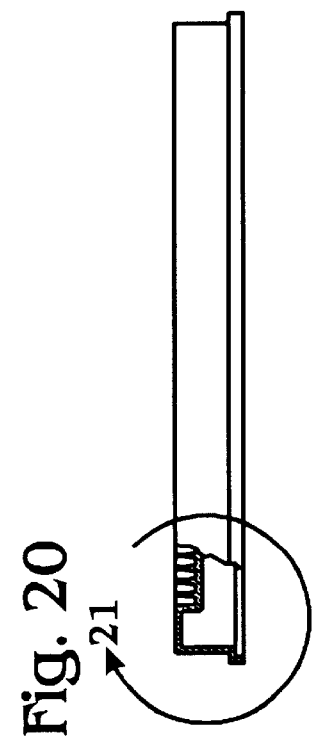
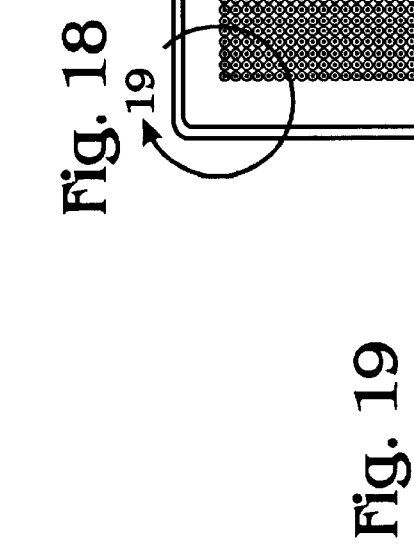
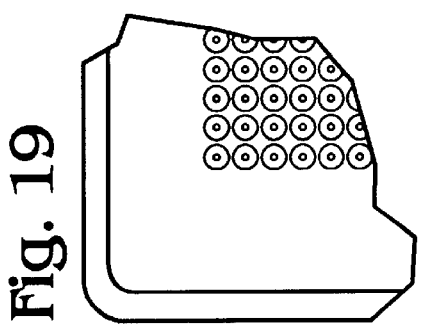
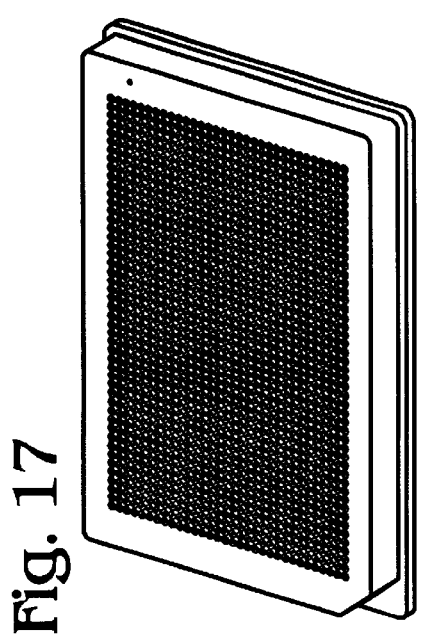
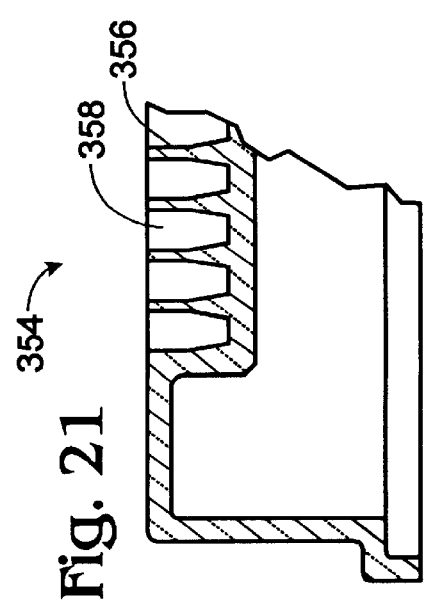

SAMPLE-HOLDING DEVICES AND SYSTEMS

CROSS-REFERENCES TO PRIORITY APPLICATIONS

This application is a continuation of PCT Patent Application Serial No. PCT/US99/08410, filed Apr. 16, 1999. The PCT application, in turn, is a continuation of and claims priority from the following U.S. patent applications: Ser. No. 09/062,472, filed Apr. 17, 1998; now U.S. Pat. No. 6,071, 748 Ser. No. 09/156,318, filed Sep. 18, 1998; now U.S. Pat. No. 6,258,326 and Ser. No. 09/160,533, filed Sep. 24, 1998 now U.S. Pat. No. 6,097,025. The PCT application, in turn, also is based upon and claims benefit under 35 U.S.C. §119 of the following U.S. provisional patent applications: Ser. No. 60/085,500, filed May 14, 1998; Ser. No. 60/089,848, filed Jun. 19, 1998; Ser. No. 60/114,209, filed Dec. 29, 1998; and Ser. No. 60/119,829, filed Feb. 12, 1999. These PCT, U.S., and U.S. provisional patent applications are each incorporated herein by reference.

CROSS-REFERENCE TO RELATED MATERIALS

This application incorporates by reference the following PCT Patent Applications: Ser. No. PCT/US98/23095, filed Oct. 30, 1998; Ser. No. PCT/US99/01656, filed Jan. 25, 1999; and Ser. No. PCT/US99/03678, filed Feb. 19, 1999.

This application incorporates by reference the following publication: JOSEPH R. LAKOWICZ, PRINCIPLES OF FLUORESCENCE SPECTROSCOPY (1983).

FIELD OF THE INVENTION

The invention relates to sample-holding devices and systems, and more particularly to sample-holding devices and systems for efficiently utilizing relatively small-volume fluid samples.

BACKGROUND OF THE INVENTION

Certain techniques in biology, chemistry, and medicine require processing large numbers of samples; such techniques include the high-throughput luminescence screening of candidate drug compounds, which may involve analyzing hundreds of thousands of samples. Processing large numbers of samples can be facilitated by packaging samples together into high-density holders, such as "microplates," so that the samples may be analyzed together in an automated device.

Microplates are substantially rectangular holders that include a plurality of sample wells for holding a plurality of samples. These sample wells typically are cylindrical in shape, although some are rectangular. These sample wells typically are disposed in rectangular arrays. The "standard" microplate includes 96 cylindrical sample wells disposed in an 8×12 rectangular array on 9 millimeter (mm) centers.

Microplates may be used in a variety of assays, including various luminescence assays. In luminescence assays, a sample is positioned in a sample well and emission light from the sample is monitored. In photoluminescence assays, emission light is stimulated by illuminating the sample with excitation light. In chemiluminescence assays, emission light is stimulated by a chemical reaction made to take place within the sample.

Although microplates are of demonstrated utility in automated screening, they suffer from a number of shortcomings. For example, sample wells in microplates and other sample holders for luminescence assays may have regions that are optically inaccessible, from which luminescence neither can be excited nor detected. Sample in such regions effectively is wasted because it does not contribute to the analysis. Wasted sample can translate into significant extra cost, particularly for assays that are performed in large numbers and that use expensive reagents. Sample wells also may have walls or other regions that are themselves detectable optically, increasing background if such regions luminesce.

SUMMARY OF THE INVENTION

The present invention provides sample holders configured to support a sample so that the shape of the sample conforms to the shape of at least a portion of a sensed volume.

The invention provides a number of new microplate designs that are useful for high-efficiency sample analysis. In one embodiment a microplate includes a frame portion, and a top portion. An array of wells are formed in the top portion. The wells are organized in a density of at least about 4 wells per 81 $mm^2$. Each well has a bottom wall that is elevated at least about 7 millimeters above a plane defined by a bottom edge of the frame.

Another microplate design has an array of conical wells organized in a density of at least about 4 wells per 81 $mm^2$.

Another embodiment has an array of conically-shaped wells, each well having a maximum volume capacity of less than about 55 microliters. A preferred small-volume well design has a volume capacity of 1–20 microliters.

Another microplate design has an array of wells in the top portion, wherein each well has a maximum volume capacity of less than about 55 microliters, and a well bottom that is elevated at least about 7 millimeters above a plane defined by a bottom edge of the frame.

A further microplate embodiment has an array of wells in the top portion, organized in a density of at least about 4 wells per 81 $m^2$. Each well has a conical portion characterized by a cone angle of at least about 8°.

Another microplate configuration has an array of wells that are conically-shaped and characterized by a cone angle $\theta$ wherein $\theta=2\arcsin(NA/n)$, NA being equal to or greater than about 0.07.

Another microplate design has an array of wells organized in a density of at least about 16 wells per 81 $mm^2$. Each well has a frusto-conical bottom portion and a substantially cylindrical upper portion.

The invention provides a system for detecting light transmitted from a sensed volume. The system comprises (1) an optical device capable of detecting light substantially exclusively from a sensed volume, and (2) a sample holder configured to support a sample so that the shape of the sample conforms to the shape of at least a portion of the sensed volume. The sample holder may be a sample well in a microplate and may have a conical or frusto-conical shape, so that the sample conforms to a portion of an hourglass-shaped sensed volume.

The invention also provides a microplate comprising (1) a frame, and (2) a plurality of frusto-conical sample wells disposed in the frame. The sample wells may be characterized by a cone angle of at least about 8°. The microplate further may include a reference fiducial that provides information to facilitate sample analysis.

The invention also provides methods for improving signal detection in luminescence assays. One such method comprises (1) selecting an optical device capable of detecting light from a sensed volume, (2) selecting a sample holder having a shape configured to conform to the shape of the sensed volume, and (3) performing a luminescence assay using the optical device and the sample holder.

The invention will be understood more readily after consideration of the drawings and the detailed description of the invention that follow.

BRIEF DESCRIPTION OF THE DRAWINGS

FIG. 17 is a perspective view of a 1536-well microplate constructed in accordance with the invention.

FIG. 18 is a top view of the microplate in FIG. 17.

FIG. 19 is an enlarged portion of the top view in FIG. 18, showing details of the sample wells.

FIG. 20 is a partially cross-sectional view of the microplate in FIG. 17.

FIG. 21 is an enlarged portion of the cross-sectional view in FIG. 20, showing details of the sample wells.

DETAILED DESCRIPTION OF THE INVENTION

The detailed description is divided into three parts: (1) overview of luminescence assays, (2) description of luminescence apparatus, and (3) description of microplates.

1. Overview of Luminescence Assays

Luminescence is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Luminescence assays are assays that use luminescence emissions from luminescent analytes to study the properties and environment of the analyte, as well as binding reactions and enzymatic activities involving the analyte, among others. In this sense, the analyte may act as a reporter to provide information about another material or target substance that may be the focus of the assay. Luminescence assays may use various aspects of the luminescence, including its intensity, polarization, and lifetime, among others. Luminescence assays also may use time-independent (steady-state) and/or time-dependent (time-resolved) properties of the luminescence. Steady-state assays generally are less complicated than time-resolved assays, but generally yield less information.

A. Intensity Assays

Luminescence intensity assays involve monitoring the intensity (or amount) of light emitted from a composition. The intensity of emitted light will depend on the extinction coefficient, quantum yield, and number of the luminescent analytes in the composition, among others. These quantities, in turn, will depend on the environment on the analyte, among others, including the proximity and efficacy of quenchers and energy transfer partners. Thus, luminescence intensity assays may be used to study binding reactions, among other applications.

B. Polarization Assays

Luminescence polarization assays involve the absorption and emission of polarized light, and typically are used to study molecular rotation. (Polarization describes the direction of light's electric field, which generally is perpendicular to the direction of light's propagation.)

Figure 1:
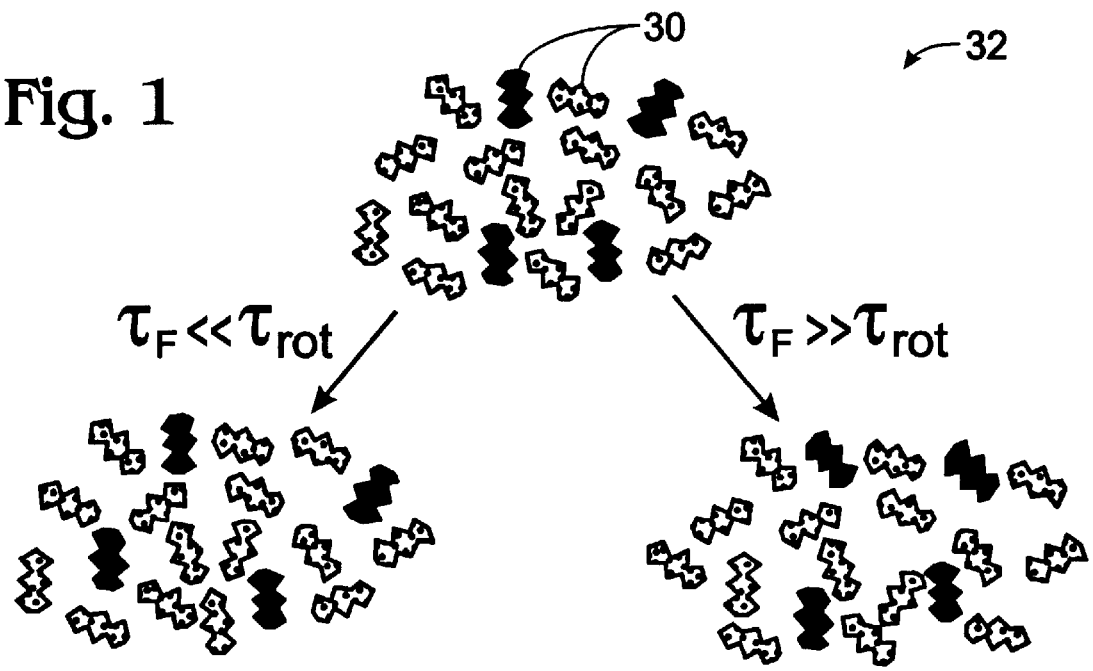
FIG. 1 is a schematic view of fluorescently labeled molecules, showing how molecular reorientation affects fluorescence polarization.

FIG. 1 is a schematic view showing how luminescence polarization is affected by molecular rotation. In a luminescence polarization assay, specific molecules 30 within a composition 32 are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent to which the total emitted light is polarized depends on the extent of molecular reorientation during the time interval between luminescence excitation and emission, which is termed the luminescence lifetime, $\tau$. The extent of molecular reorientation in turn depends on the luminescence lifetime and the size, shape, and environment of the reorienting molecule. Thus, luminescence polarization assays may be used to quantify binding reactions and enzymatic activity, among other applications. In particular, molecules rotate via diffusion with a rotational correlation time $\tau_{rot}$ that is proportional to their size. Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_\| - I_\perp}{I_\| + I_\perp} \quad (1)$$

Here, P is the polarization, $I_\|$ is the intensity of luminescence polarized parallel to the polarization of the excitation light, and $I_\perp$ is the intensity of luminescence polarized perpendicular to the polarization of the excitation light. If there is little rotation between excitation and emission, $I_\|$ will be relatively large, $I_\|$ will be relatively small, and P will be close to one. (P may be less than one even if there is no rotation; for example, P will be less than one if the absorption and emission dipoles are not parallel.) In contrast, if there is significant rotation between absorption and emission, $I_\|$ will be comparable to $I_\perp$, and P will be close to zero. Polarization often is reported in milli-P units (1000×P), which will range between 0 and 1000, because P will range between zero and one.

Polarization also may be described using other equivalent quantities, such as anisotropy. The relationship between anisotropy and intensity is expressed by the following equation:

$$r = \frac{I_\| - I_\perp}{I_\| + 2I_\perp} \quad (2)$$

Here, r is the anisotropy. Polarization and anisotropy include the same information, although anisotropy may be more simply expressed for systems containing more than one luminophore. In the description and claims that follow, these terms may be used interchangeably, and a generic reference to one should be understood to imply a generic reference to the other.

The relationship between polarization and rotation is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \quad (3)$$

Here, $P_0$ is the polarization in the absence of molecular motion (intrinsic polarization), $\tau$ is the luminescence lifetime (inverse decay rate) as described above, and $\tau_{rot}$ is the rotational correlation time (inverse rotational rate) as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 Dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 Daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 Daltons and 4,000,000 Daltons.

C. Time-Resolved Assays

Time-resolved assays involve measuring the time course of luminescence emission. Time-resolved assays may be conducted in the time domain or in the frequency domain, both of which are functionally equivalent. In a time-domain measurement, the time course of luminescence is monitored directly. Typically, a composition containing a luminescent analyte is illuminated using a narrow pulse of light, and the time dependence of the intensity of the resulting luminescence emission is observed, although other protocols also may be used. For a simple molecule, the luminescence commonly follows a single-exponential decay.

In a frequency-domain measurement, the time course of luminescence is monitored indirectly, in frequency space. Typically, the composition is illuminated using light whose intensity is modulated sinusoidally at a single modulation frequency f, although other protocols (such as transforming time-domain data into the frequency domain) also may be used. The intensity of the resulting luminescence emission is modulated at the same frequency as the excitation light. However, the emission will lag the excitation by a phase angle (phase) $\phi$, and the intensity of the emission will be demodulated relative to the intensity of the excitation by a demodulation factor (modulation) M.

Figure 2:
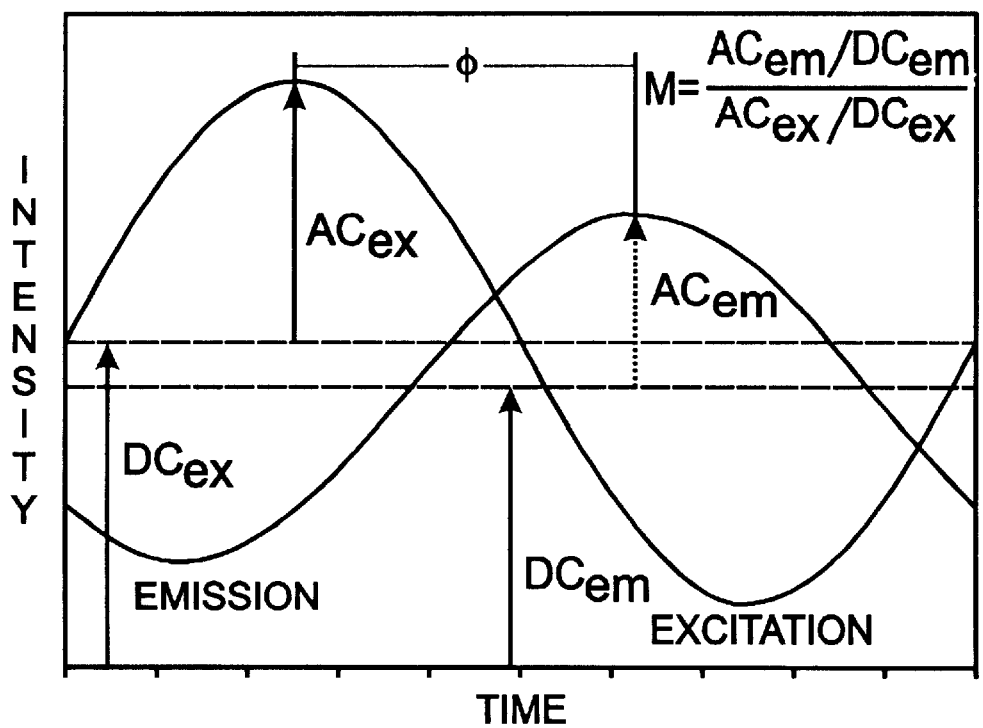
FIG. 2 is a schematic view of a frequency-domain time-resolved measurement, showing the definitions of phase angle (phase) φ and demodulation factor (modulation) M.

FIG. 2 shows the relationship between emission and excitation in a single-frequency frequency-domain experiment. The phase $\phi$ is the phase difference between the excitation and emission. The modulation M is the ratio of the AC amplitude to the DC amplitude for the emission, relative to the ratio of the AC amplitude to the DC amplitude for the excitation. The phase and modulation are related to the luminescence lifetime $\tau$ by Equations 4 and 5.

$$\omega\tau = \tan(\phi) \quad (4)$$

$$\omega\tau = \sqrt{\frac{1}{M^2} - 1} \quad (5)$$

Here $\omega$ is the angular modulation frequency, which equals $2\pi$ times the modulation frequency. For maximum sensitivity, the angular modulation frequency should be roughly the inverse of the luminescence lifetime. Lifetimes of interest in high-throughput screening vary from less than 1 nanosecond to greater than 10 microseconds. Therefore, instruments for high-throughput screening should be able to cover modulation frequencies from 20 kHz to 200 MHz.

D. Strengths and Weaknesses of Luminescence Assays

Luminescence methods have several significant potential strengths. First, luminescence methods may be very sensitive, because modern detectors, such as photomultiplier tubes (PMTs) and charge-coupled devices (CCDs), can detect very low levels of light. Second, luminescence methods may be very selective, because the luminescence signal may come almost exclusively from the luminophore.

Luminescence assays also have several significant potential weaknesses. First, luminescence from the analyte might be perturbed in some way, distorting results. For example, if a luminescent analyte binds to the walls of a sample holder during a fluorescence polarization assay, the analyte will be unable to rotate, spuriously increasing the polarization. Second, luminescence may arise from sources other than the analyte, contaminating the signal. For example, luminescence may arise from the sample holder, including glass coverslips and plastic microplates.

2. Description of Luminescence Apparatus

FIGS. 3–6 show an apparatus 90 for detecting light emitted by an analyte in a composition. Apparatus 90 includes (1) a stage for supporting the composition, (2) one or more light sources for delivering light to a composition, (3) one or more detectors for receiving light transmitted from the composition and converting it to a signal, (4) first and second optical relay structures for relaying light between the light source, composition, and detector, and (5) a processor for analyzing the signal from the detector. All or only a subset of these components may be used in any given application.

Apparatus 90 may be used for a variety of assays, including but not limited to the assays described above. Components of the optical system may be chosen to optimize sensitivity and dynamic range for each assay supported by the apparatus. Toward this end, optical components with low intrinsic luminescence are preferred. In addition, some components may be shared by different modes, whereas other components may be unique to a particular mode. For example, in apparatus 90, photoluminescence intensity and steady-state photoluminescence polarization modes share a light source; time-resolved luminescence modes use their own light source; and chemiluminescence modes do not use a light source. Similarly, photoluminescence and chemiluminescence modes use different detectors.

The remainder of this section is divided into five subsections: (A) photoluminescence optical system, (B) chemiluminescence optical system, (C) housing, (D) alternative apparatus, and (E) methods.

A. Photoluminescence Optical System

As configured here, apparatus 90 includes a continuous light source 100 and a time-modulated light source 102. Apparatus 90 includes light source slots 103a–d for four light sources, although other numbers of light source slots and light sources also could be provided. Light source slots 103a–d function as housings that may surround at least a portion of each light source, providing some protection from radiation and explosion. The direction of light transmission through the photoluminescence optical system is indicated by arrows.

Continuous source 100 provides light for photoluminescence intensity and steady-state photoluminescence polarization assays. Continuous light source 100 may include arc lamps, lasers, laser diodes, and light-emitting diodes (LEDs), among others. A preferred continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, increasing sensitivity and reducing read times. Apparatus 90 may include a modulator mechanism configured to vary the intensity of light incident on the composition without varying the intensity of light produced by the light source.

Time-modulated source 102 provides light for time-resolved photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers, electronically modulated lasers and LEDs, and continuous lamps whose intensity can be modulated extrinsically using a Pockels cell, Kerr cell, or other mechanism. The latter sources are especially well suited for frequency-domain measurements.

In apparatus 90, continuous source 100 and time-modulated source 102 produce multichromatic, unpolarized, and incoherent light. Continuous source 100 produces substantially continuous illumination, whereas time-modulated source 102 produces time-modulated illumination. Light from these light sources may be delivered to the sample without modification, or it may be filtered to alter its intensity, spectrum, polarization, or other properties.

Light produced by the light sources follows an excitation optical path to an examination site. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. In apparatus 90, spectrum is altered by an excitation interference filter 104, which selectively transmits light of preselected wavelengths and selectively absorbs light of other wavelengths. For convenience, excitation interference filters 104 may be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 106 may be mounted in the optical path of some light source slots 103a,b, but not other light source slots 103c,d.

Light next passes through an excitation optical shuttle (or switch) 108, which positions an excitation fiber optic cable 110a,b in front of the appropriate light source to deliver light to top or bottom optics heads 112a,b, respectively. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In apparatus 90, polarization is altered by excitation polarizers 114, which are included only with top optics head 112a; however, such polarizers also can be included with bottom optics head 112b for bottom reading. Excitation polarization filters 114 may include an s-polarizer S that passes only s-polarized light, a p-polarizer P that passes only p-polarized light, and a blank O that passes substantially all light. Excitation polarizers 114 also may include a standard or ferro-electric liquid crystal display (LCD) polarization switching system. Such a system is faster and more economical than a mechanical switcher. Excitation polarizers 114 also may include a continuous mode LCD polarization rotator with synchronous detection to increase the signal-to-noise ratio in polarization assays. Excitation polarizers 114 may be included in light sources, such as certain lasers, that intrinsically produce polarized light.

Figure 5:
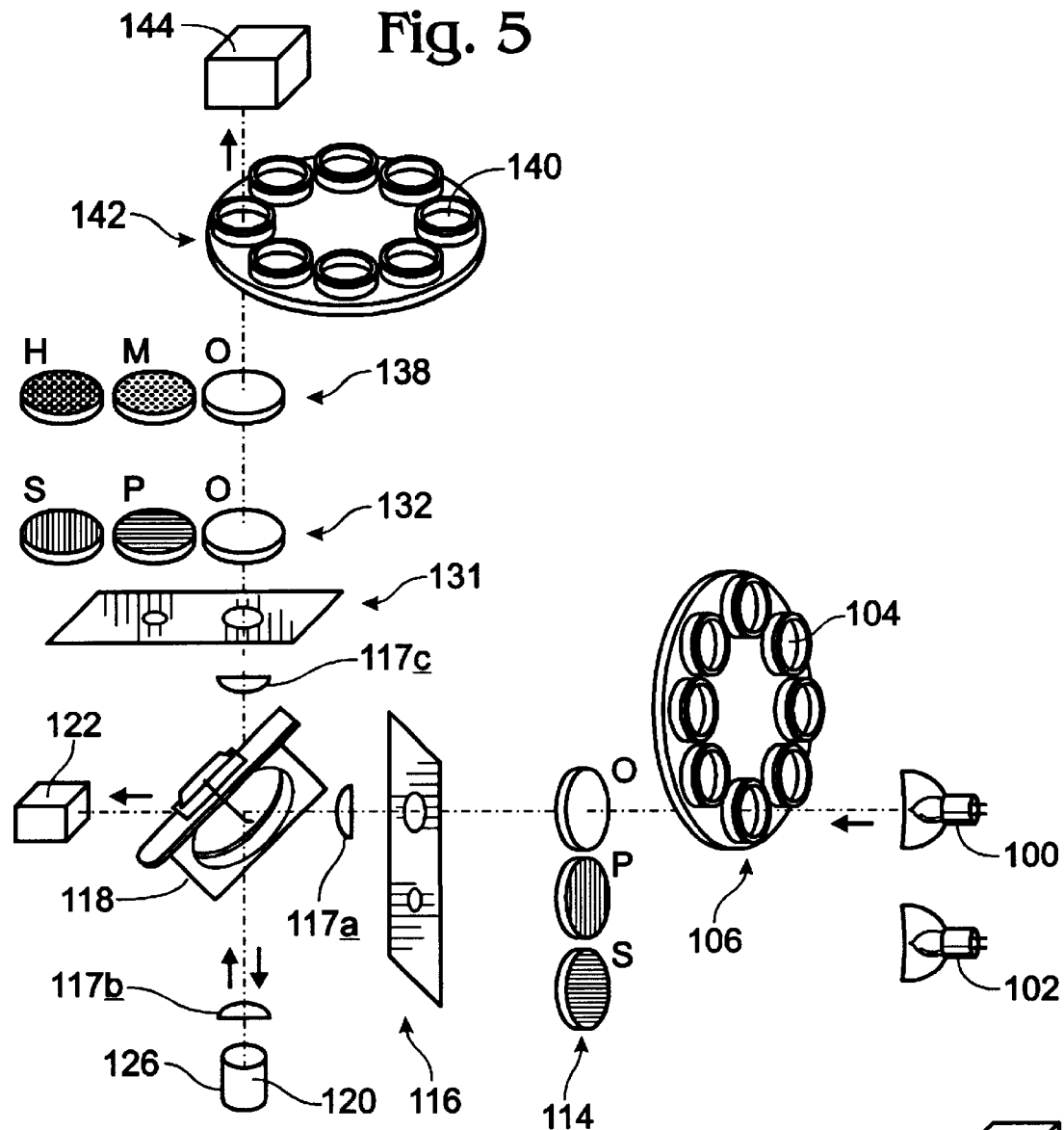
FIG. 5 is a schematic view of photoluminescence optical components from the apparatus of FIG. 3.

Light at one or both optics heads also may pass through an excitation "confocal optics element," which generally comprises any mechanism for focusing light into a "sensed volume." In apparatus 90, the confocal optics element includes a set of lenses 117a–c and an excitation aperture 116 placed in an image plane conjugate to the sensed volume, as shown in FIG. 5. Aperture 116 may be implemented directly, as an aperture, or indirectly, as the end of a fiber optic cable. Preferred apertures have diameters of 1 mm and 1.5 mm. Lenses 117a,b project an image of aperture 116 onto the sample, so that only a preselected or sensed volume of the sample is illuminated. The area of illumination will have a diameter corresponding to the diameter of the excitation aperture.

Light traveling through the optics heads is reflected and transmitted through a beamsplitter 118, which delivers reflected light to a composition 120 and transmitted light to a light monitor 122. Reflected and transmitted light both pass through lens 117b, which is operatively positioned between beamsplitter 118 and composition 120.

Beamsplitter 118 is used to direct excitation light toward the sample and light monitor, and to direct emission light toward the detector. The beamsplitter is changeable, so that it may be optimized for different assay modes or compositions. If a large number or variety of luminescent molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable emission light to the detector. If one or a few related luminescent molecules are to be studied, the beamsplitter needs only to be able to accommodate light at a limited number of wavelengths; in this case, a "dichroic" or "multichroic" beamsplitter is optimal. Such a beamsplitter can be designed with cutoff wavelengths for the appropriate set of molecules and will reflect most or substantially all of the excitation and background light, while transmitting most or substantially all of the emission light. This is possible because the reflectivity and transmissivity of the beamsplitter can be varied with wavelength.

Light monitor 122 is used to correct for fluctuations in the intensity of light provided by the light sources; such corrections may be performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The composition (or sample) may be held in a sample holder supported by a stage 123. The composition can include compounds, mixtures, surfaces, solutions, emulsions, suspensions, cell cultures, fermentation cultures, cells, tissues, secretions, and/or derivatives and/or extracts thereof. Analysis of the composition may involve measuring the presence, concentration, or physical properties (including interactions) of a photoluminescent analyte in such a composition. The sample holder can include microplates, biochips, or any array of samples in a known format. In apparatus 90, the preferred sample holder is a microplate 124, which includes a plurality of microplate wells 126 for holding compositions. Composition may refer to the contents of a single microplate well, or several microplate wells, depending on the assay. In some embodiments, such as a portable apparatus, the stage may be intrinsic to the instrument.

The sensed volume typically has an hourglass shape, with a cone angle of about 25° and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample holder may be matched to the size and shape of the sensed volume.

Figure 3:
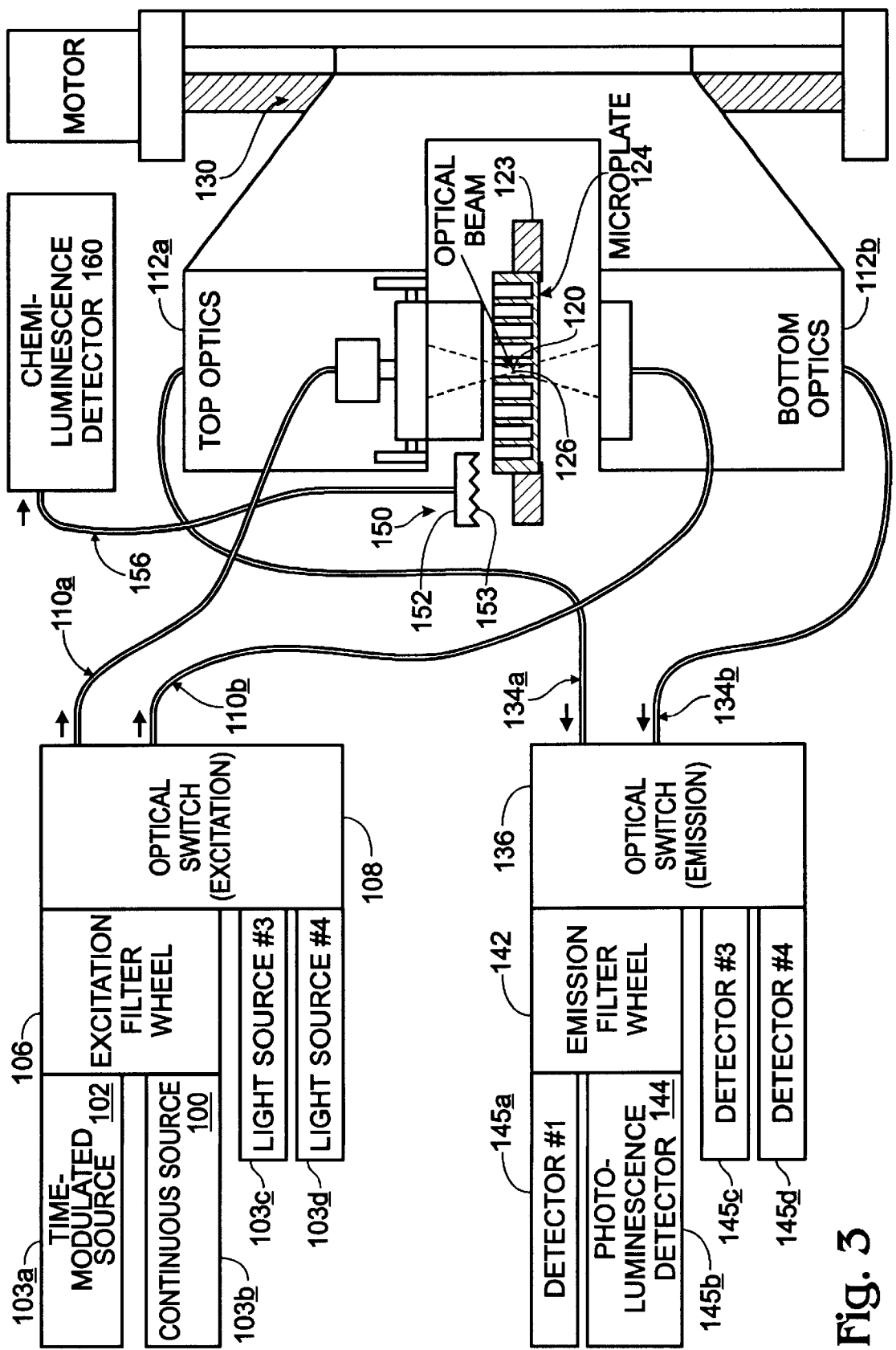
FIG. 3 is a schematic view of an apparatus for detecting light.
Figure 4:
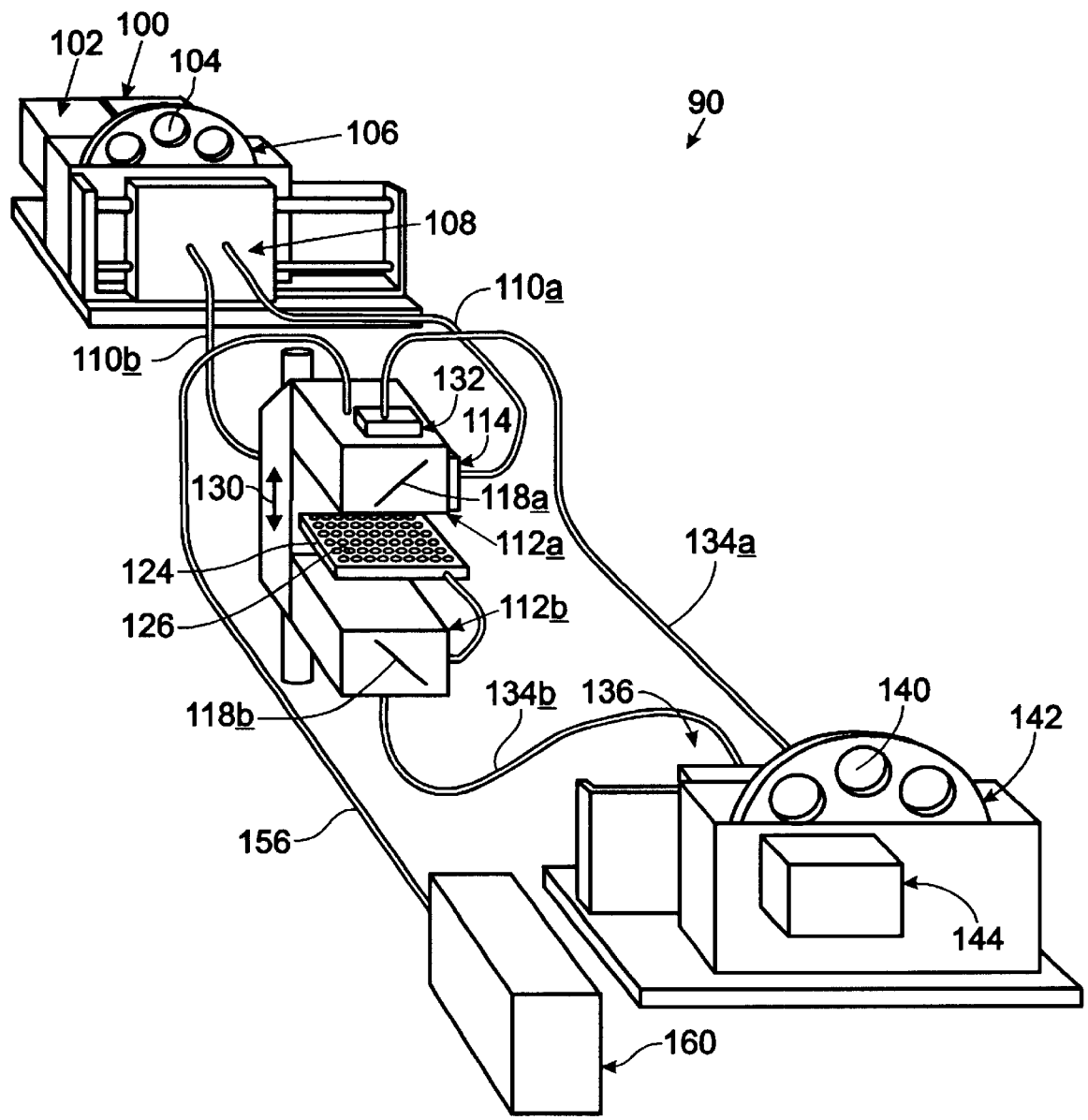
FIG. 4 is a partially schematic perspective view of the apparatus of FIG. 3.

The position of the sensed volume can be moved precisely within the composition to optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In apparatus 90, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 3 and 4. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection (1) and (4) is referred to as "epi" and is preferred for photoluminescence assays. Opposite-side illumination and detection (2) and (3) is referred to as "trans" and is preferred for absorbance assays. In apparatus 90, epi modes are supported, so the excitation and emission light travel the same path in the optics head, albeit in opposite or anti-parallel directions. However, trans modes also could be supported and would be essential for absorbance assays. Generally, top optics can be used with any sample holder having an open top, whereas bottom optics can be used only with sample holders having optically transparent bottoms, such as glass or thin plastic bottoms.

Light is transmitted by the composition in multiple directions. A portion of the transmitted light will follow an emission pathway to a detector. Transmitted light passes through lens 117c and may pass through an emission aperture 131 and/or an emission polarizer 132. In apparatus 90, the emission aperture is placed in an image plane conjugate to the sensed volume and transmits light substantially exclusively from this sensed volume. In apparatus 90, the emission apertures in the top and bottom optical systems are the same size as the associated excitation apertures, although other sizes also may be used. The emission polarizers are included only with top optics head 112a. The emission aperture and emission polarizer are substantially similar to their excitation counterparts. Emission polarizer 132 may be included in detectors that intrinsically detect the polarization of light.

Excitation polarizers 114 and emission polarizers 132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In apparatus 90, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In apparatus 90, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters may be changed manually or automatically, for example, by using a filter wheel. Intensity filters also may divert a portion of the light away from the sample without absorption. Examples include beam splitters, which transmit some light along one path and reflect other light along another path, and Pockels cells, which deflect light along different paths through diffraction. Examples also include hot mirrors or windows that transmit light of some wavelengths and absorb light of other wavelengths.

Light next may pass through an emission interference filter 140, which may be housed in an emission filter wheel 142. In apparatus 90, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance and photoluminescence assays. In apparatus 90, there is one photoluminescence detector 144, which detects light from all photoluminescence modes. A preferred detector is a photomultiplier tube (PMT). Apparatus 90 includes detector slots 145a–d for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, and/or (3) imaging modes, among others, as described below.

B. Chemiluminescence Optical System

Figure 6:
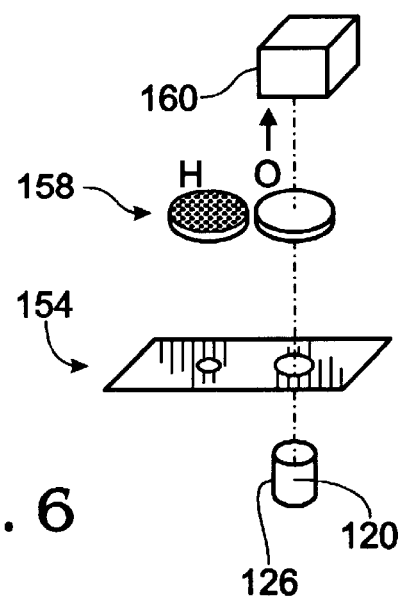
FIG. 6 is a schematic view of chemiluminescence optical components from the apparatus of FIG. 3.

FIGS. 3, 4, and 6 show the chemiluminescence optical system of apparatus 50. Because chemiluminescence follows a chemical event rather than the absorption of light, the chemiluminescence optical system does not require a light source or other excitation optical components. Instead, the chemiluminescence optical system requires only selected emission optical components. In apparatus 50, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the photoluminescence optical system. The chemiluminescence optical system also can be used for other assay modes that do not require illumination, such as electrochemiluminescence.

The chemiluminescence optical path begins with a chemiluminescent composition 120 held in a sample holder 126. The composition and sample holder are analogous to those used in photoluminescence assays; however, analysis of the composition involves measuring the intensity of light generated by a chemiluminescence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample holder. A portion of the light transmitted through the top of the well is collected using a chemiluminescence head 150, as shown in FIG. 3, and will follow a chemiluminescence optical pathway to a detector. The direction of light transmission through the chemiluminescence optical system is indicated by arrows.

The chemiluminescence head includes a nonconfocal mechanism for transmitting light from a sensed volume within the composition. Detecting from a sensed volume reduces contributions to the chemiluminescence signal resulting from "cross talk," which is pickup from neighboring wells. The nonconfocal mechanism includes a chemiluminescence baffle 152, which includes rugosities 153 that absorb or reflect light from other wells. The nonconfocal mechanism also includes a chemiluminescence aperture 154 that further confines detection to a sensed volume.

Light next passes through a chemiluminescence fiber optic cable 156, which may be replaced by any suitable mechanism for directing light from the composition toward the detector. Fiber optic cable 156 is analogous to excitation and emission fiber optic cables 110a,b and 134a,b in the photoluminescence optical system. Fiber optic cable 156 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In apparatus 50, intensity is altered by chemiluminescence neutral density filters 158. Light also may pass through other filters, if desired.

Light last passes to a detector, which converts light into signals that may be processed by the apparatus. In apparatus 50, there is one chemiluminescence detector 160. This detector may be selected to optimize detection of blue/green light, which is the type most often produced in chemiluminescence. A preferred detection is a photomultiplier tube, selected for high quantum efficiency and low dark count at chemiluminescence wavelengths (400–500 nanometers).

C. Housing

Figure 7:
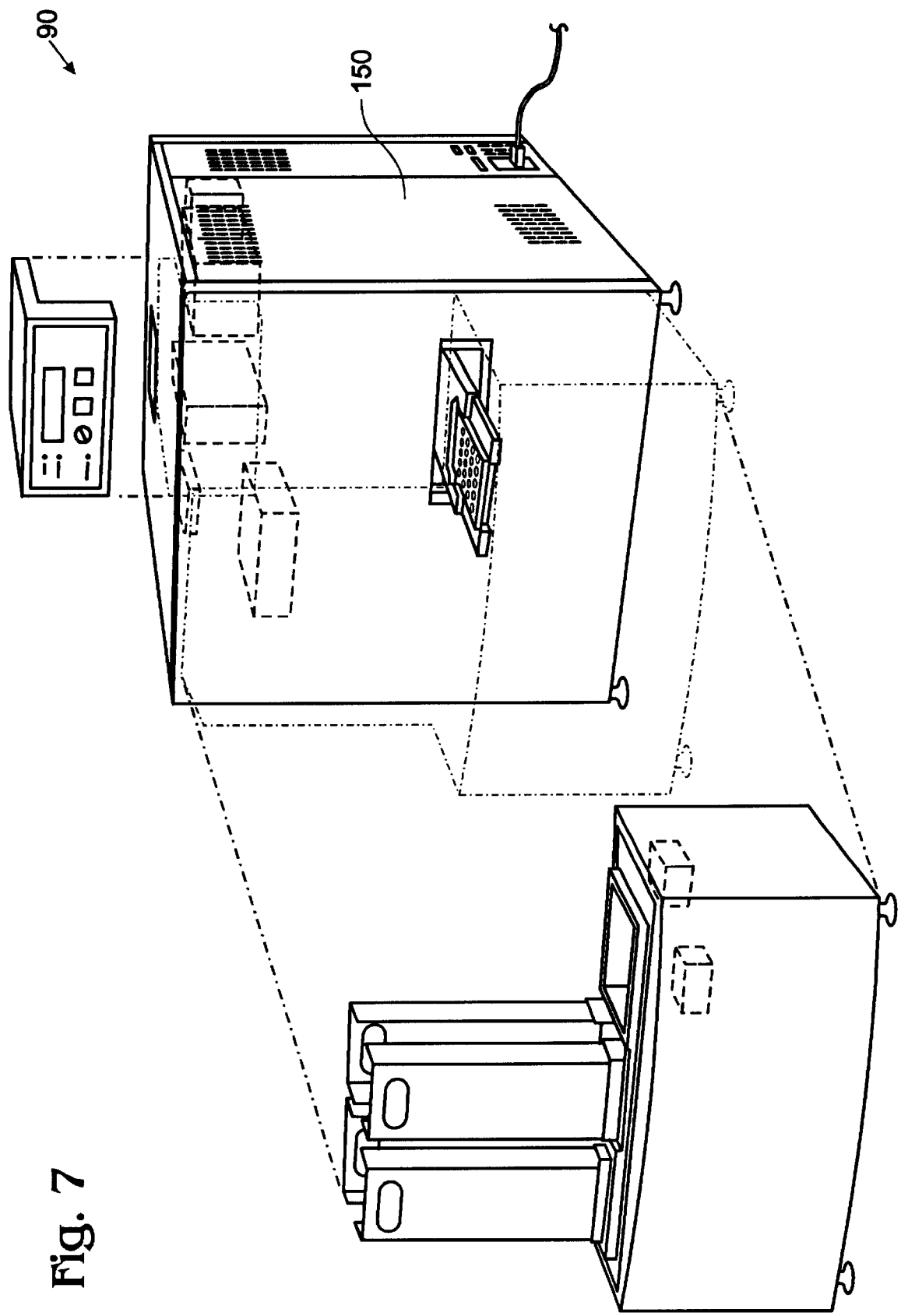
FIG. 7 is a partially exploded perspective view of a housing for the apparatus of FIGS. 3 and 4.

FIG. 7 shows a housing 150 and other accessories for the apparatus of FIGS. 3–6. Housing 150 substantially encloses the apparatus, forming (together with light source slots 103a–d) two protective layers around the continuous high color temperature xenon arc lamp. Housing 150 permits automated sample loading and switching among light sources and detectors, further protecting the operator from the xenon arc lamp and other components of the system.

D. Alternative Apparatus

Figure 8:
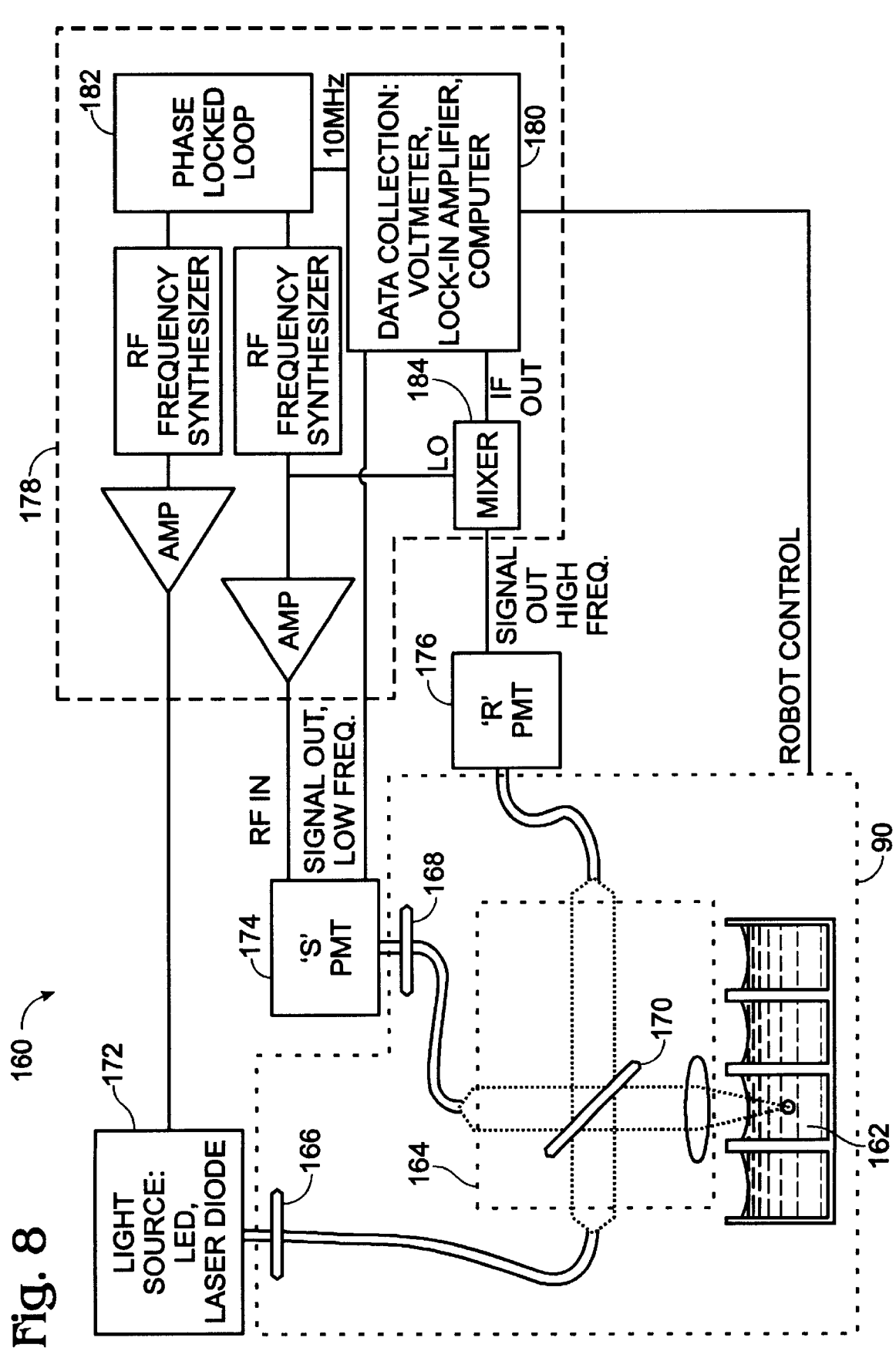
FIG. 8 is a schematic view of an alternative apparatus for detecting light in accordance with the invention.

FIG. 8 shows an alternative apparatus 160 for detecting light emitted by an analyte in a composition 162. Apparatus 160 includes substantial portions of apparatus 90, including its fiber-optic-coupled optics head 164, excitation 166 and emission 168 filters, dichroic beam splitter 170, and mechanisms for sample positioning and focus control. However, apparatus 160 also may include alternative light sources 172, alternative sample ('S') 174 and reference ('R') 176 detectors, and alternative detection electronics 178. In FIG. 8, alternative components 172–178 are shown outside apparatus 90, but they readily may be included inside housing 150 of apparatus 90, if desired.

Apparatus 160 may excite luminescence in various ways, such as using an LED or laser diode light source. For example, analytes absorbing blue light may be excited using a NICHIA-brand bright-blue LED (Model Number NSPB500; Mountville, Pa.). This LED produces broad-spectrum excitation light, so excitation filter 166 typically is used to block the red edge of the spectrum. If analytes are excited using a laser diode, an excitation filter is not necessary.

Apparatus 160 may detect luminescence and convert it to a signal in various ways. Luminescence can be detected using sample PMT 174, which may be an ISS-brand gain-modulated PMT (Champaign, Ill.). High-frequency luminescence can be frequency down-converted to a low-frequency signal using a technique called heterodyning. The phase and modulation of the low-frequency signal can be determined using a lock-in amplifier 180, such as a STANFORD RESEARCH SYSTEMS brand lock-in amplifier (Model Number SR830; Sunnyvale, Calif.). Lock-in amplifier 180 is phase locked using a phase-locked loop 182 to the modulation frequency of light source 172. To correct for drift in the light source, the output of light source 172 may be monitored using reference PMT 176, which may be a HAMAMATSU-brand PMT (Model Number H6780; Bridgewater, N.J.). If reference PMT 176 can respond to high-frequency signals, the heterodyning step can be performed using an external mixer 184. The phase and modulation of reference PMT 176 also may be captured by lock-in amplifier 180 and used to normalize the signal from sample PMT 174.

A computer or processor controls the apparatus, including the external components. The computer also directs sample handling and data collection. Generally, phase and modulation data are collected at one or more frequencies appropriate for the lifetime of the analyte. In some cases, phase and modulation may be measured at one or a few frequencies and processed by the computer or processor to help reduce detected background.

Yet other apparatus or optical devices having yet other combinations of components also may be used in the invention, although some embodiments require that the other apparatus also be capable of detecting light substantially exclusively from a sensed volume.

E. Methods

Apparatus 90 and apparatus 160 both may be used to conduct a variety of steady-state and time-resolved luminescence assays. Steady-state assays measure luminescence under constant illumination, using the continuous light source. Time-resolved polarization assays measure luminescence as a function of time, using either the continuous light source, with its intensity appropriately modulated, or the time-varying light source.

Intensity assays may be conducted by monitoring the intensity of the luminescence emitted by the composition.

Polarization assays may be conducted as follows. Excitation light from the continuous light source is directed through an excitation filter, low-luminescence fiber optic cable, and excitation polarization filter. Excitation light then is directed to a beamsplitter, which reflects most of the light onto a composition and transmits a little of the light into a light monitor. Emitted light from the composition is directed back through the beamsplitter and then is directed through another low-luminescence fiber optic cable, an emission filter, and a polarization filter (in either the S or P orientation) before detection by a photomultiplier tube. Two measurements are performed for each composition, one with excitation and emission polarizers aligned and one with excitation and emission polarizers crossed. Either polarizer may be static or dynamic, and either polarizer may be set in the S or P orientation, although typically the excitation polarizer is set in the S orientation.

Additional luminescence assays, including fluorescence resonance energy transfer (FRET), fluorescence lifetime (FLT), total internal reflection fluorescence (TIR), fluorescence correlation spectroscopy (FCS), and fluorescence recovery after photobleaching (FRAP), as well as their phosphorescence analogs, may be conducted using procedures outlined in JOSEPH R. LAKOWICZ, PRINCIPLES OF FLUORESCENCE SPECTROSCOPY (1983) and/or generally known to persons of ordinary skill in the art.

3. Description of Microplates

This section is divided into ten subsections: (A) 96-well microplates, (B) 384-well microplates, (C) 1536-well microplates, (D) families of microplates, (E) application of sensed volumes, (F) factors affecting sensed volume, (G) reference fiducials, (H) prevention of formation and trapping of bubbles, (I) composition of microplates, and (J) methods.

A. 96-Well Microplates

Figure 9:
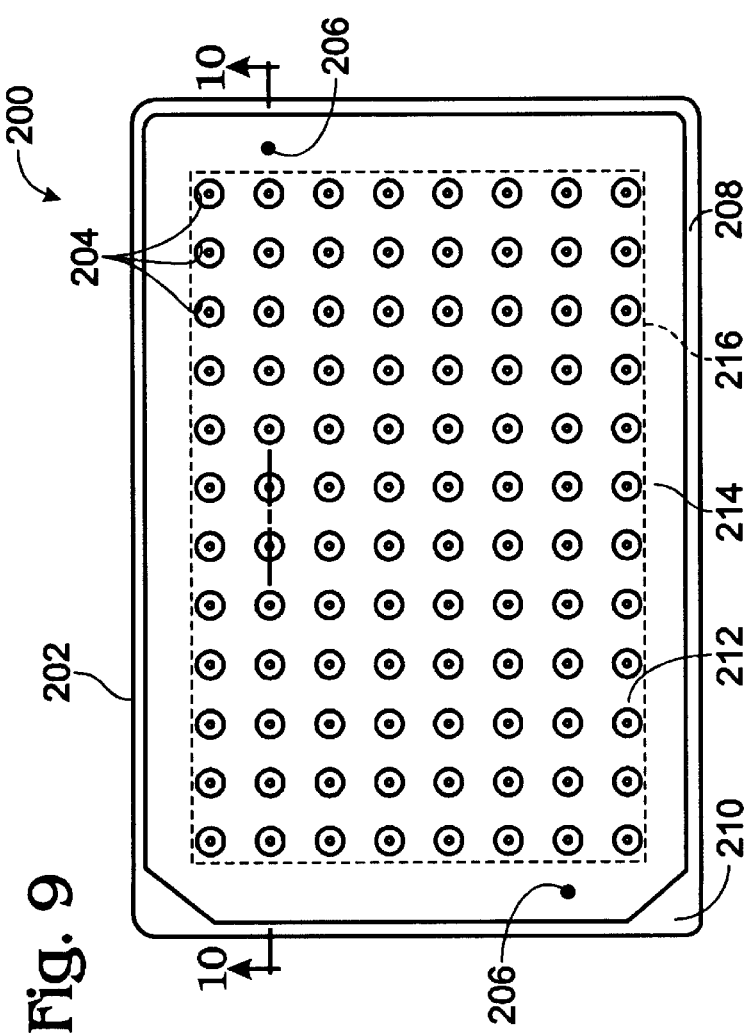
FIG. 9 is a top view of a 96-well microplate constructed in accordance with the invention.

FIG. 9 is a top view of a 96-well microplate 200 constructed in accordance with the invention. Microplate 200 includes a frame 202 and a plurality of sample wells 204 disposed in the frame. In some embodiments, microplate 200 also includes one or more reference fiducials 206 disposed in the frame.

Frame 202 is the main structural component of microplate 200. The frame may have various shapes and various dimensions. In microplate 200, frame 202 is substantially rectangular, with a major dimension X of about 127.8 mm and a minor dimension Y of about 85.5 mm. Frame 202 may be adapted for ease of use and manufacture. For example, frame 202 may include a base 208 to facilitate handling and/or stacking, and frame 202 may include notches 210 to facilitate receiving a protective lid. Frame 202 may be constructed of a material, such as a thermoplastic, that is sturdy enough for repeated, rugged use and yet minimally photoluminescent to reduce background upon illumination.

Frame 202 includes a sample well region 212 and an edge region 214 forming a perimeter 216 around the sample well region. Sample wells may be disposed in the sample well region in various configurations. In microplate 200, sample wells 204 are disposed in sample well region 212 in a substantially rectangular 8×12 array, with a pitch (i.e., center-to-center interwell spacing) along both X and Y of about 9 mm. This pitch corresponds to a density of wells of about one well per 81 mm$^2$. Reference fiducials may be disposed in the sample well region and/or the edge region in various configurations. In microplate 200, reference fiducials 206 are disposed in edge region 214, substantially aligned with a row of sample wells along the X dimension. Reference fiducials preferentially are positioned in corners of the microplate, near where optical analysis begins, so that they may quickly be identified and analyzed. Reference fiducials may be positioned in rotationally symmetric positions, so that microplates may be loaded into an optical device and analyzed backwards without difficulty.

Figure 10:
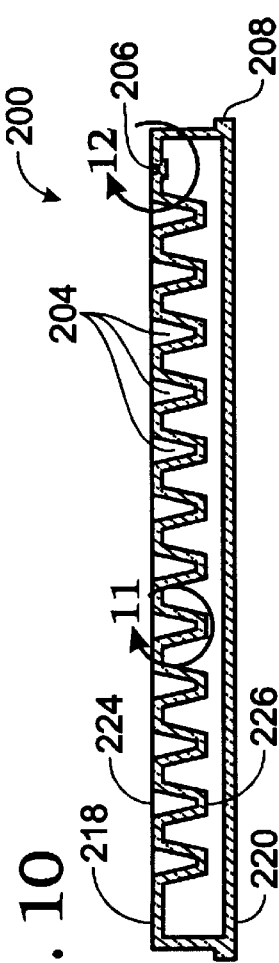
FIG. 10 is a cross-sectional view of the microplate in FIG. 9, taken generally along line 10—10 in FIG. 9.
Figure 16:
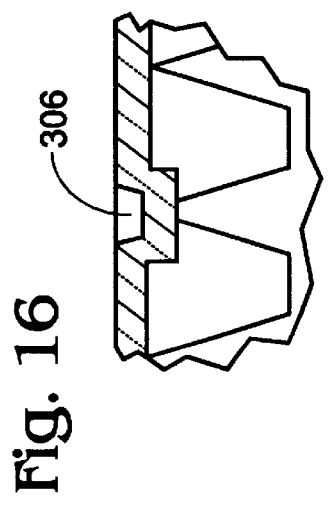
FIG. 16 is an enlarged cross-sectional view of the microplate in FIG. 13, taken generally along line 16—16 in FIG. 13, showing details of a reference fiducial.
Figure 15:
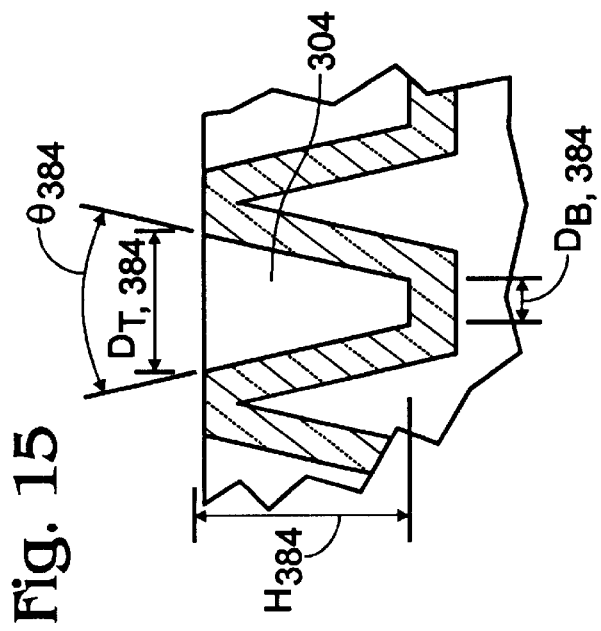
FIG. 15 is an enlarged portion of the cross-sectional view in FIG. 13, showing details of a sample well.
Figure 13:
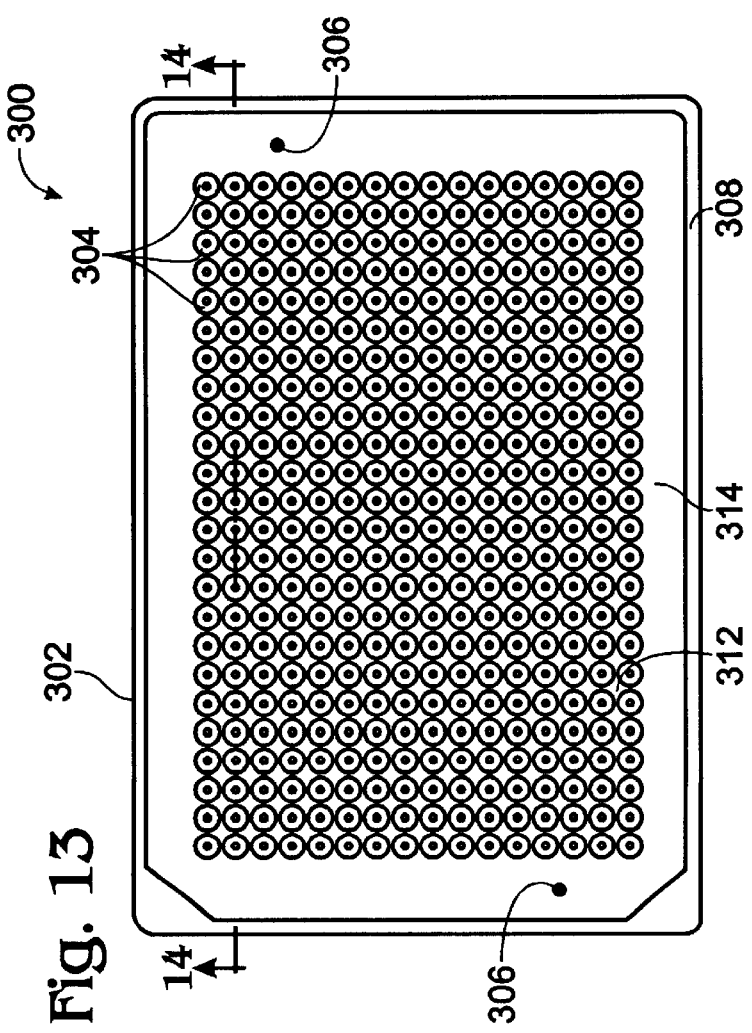
FIG. 13 is a top view of a 384-well microplate constructed in accordance with the invention.
Figure 14:
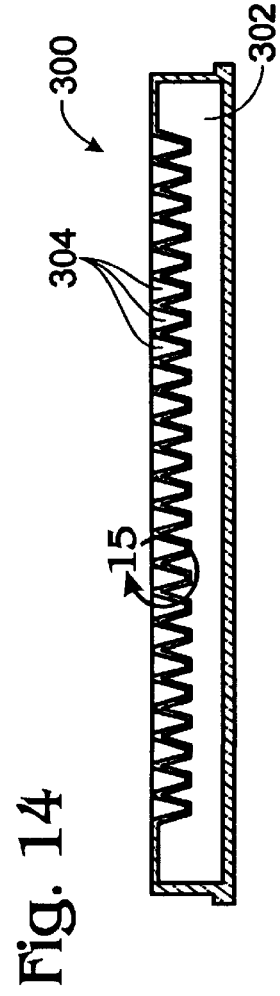
FIG. 14 is a cross-sectional view of the microplate in FIG. 13, taken generally along line 14—14 in FIG. 13.

FIG. 10 is a cross-sectional view of microplate 200, showing sample wells 204, a reference fiducial 206, and base 208. In microplate 200, frame 202 has a top 218, a substantially parallel bottom 220, and substantially perpendicular sides 222. Top 218 may have various shapes. However, top 218 typically is flat, although top 218 may be surrounded by a raised edge to facilitate stacking. Frame 202 has a height H of about 12 mm, corresponding generally to the separation between top 218 and bottom 220. This height is large enough to facilitate handling by sample handlers and/or a stage, and yet small enough to permit optical analysis of the entire well. Sample wells 204 are disposed with open, optically transparent ends 224 directed toward top 218, and closed, optically opaque ends 226 directed toward bottom 220. In some embodiments, optically opaque ends 226 may be replaced by optically transparent ends to permit bottom illumination and/or detection. Reference fiducial 206 is disposed on top 218, although reference fiducials also may be disposed on bottom 220 and/or sides 222.

Figure 11:
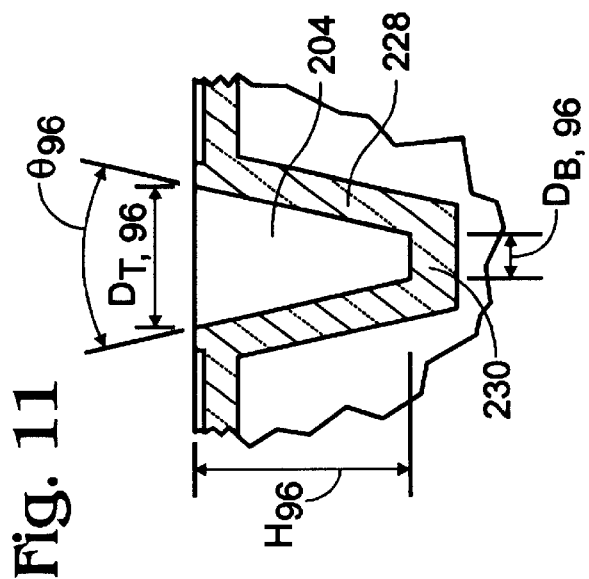
FIG. 11 is a first enlarged portion of the cross-sectional view in FIG. 10, showing details of a sample well.

FIG. 11 is a first enlarged portion of the cross-sectional view in FIG. 10, showing details of sample wells 204. Sample wells may have various shapes and various dimensions, as described in detail in subsequent sections. In microplate 200, sample wells 204 are substantially frusto-conical, with substantially straight side walls 228 and a substantially flat bottom wall 230. In microplate 200, optically opaque ends 226 are positioned about 6.7 mm below top 218, and about 5.3 mm above bottom 220. Sample well 204 is characterized by a top diameter $D_{T,96}$, a bottom diameter $D_{B,96}$, a height $H_{96}$, and a cone angle $\theta_{96}$. Here, $\theta_{96}$ is the included angle between side walls 228. In microplate 200, $D_{T,96}$ is about 4.5 mm, $D_{B,96}$ is about 1.5 mm, $H_{96}$ is about 6.7 mm, and $\theta_{96}$ is about 25.4°. Sample well 204 has a total volume of about 50 μL, and a smallest practical working volume of about 1–20 μL.

Figure 12:
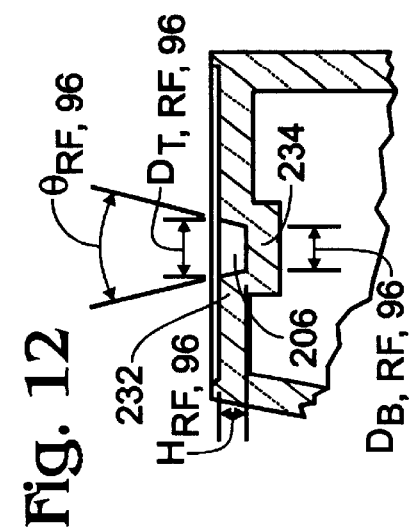
FIG. 12 is a second enlarged portion of the cross-sectional view in FIG. 10, showing details of a reference fiducial.

FIG. 12 is a second enlarged portion of the cross-sectional view in FIG. 10, showing details of reference fiducial 206. Reference fiducials may have various shapes and various dimensions, as described in detail in subsequent sections. In microplate 200, reference fiducial 206 is substantially frusto-conical, with substantially straight side walls 232 and a substantially flat bottom wall 234. Reference fiducial 206 is characterized by a top diameter $D_{T,RF,96}$, a bottom diameter $D_{B,RF,96}$, a height $H_{RF,96}$, and a cone angle $\theta_{RF,96}$. Here, $D_{RF,96}$ and $\theta_{RF,96}$ are substantially equal to $D_{B,96}$ and $\theta_{96}$, the corresponding values for sample well 204. $H_{96}$ is about 1 mm, and $D_{T,RF,96}$ is specified by the other parameters.

B. 384-Well Microplates

FIGS. 13–16 are views of a 384-well microplate 300 constructed in accordance with the invention. Microplate 300 is similar to microplate 200 and includes a frame 302 and a plurality of sample wells 304 disposed in a sample well region 312 of the frame. In some embodiments, microplate 300 also includes one or more reference fiducials 306 disposed in an edge region 314 or other region of the frame.

The external dimensions of microplate 300 are similar to the external dimensions of microplate 200. However, the density of sample wells in microplate 300 is four times higher than the density of sample wells in microplate 200. Consequently, the pitch (i.e., the center-to-center interwell spacing) in microplate 300 is about 4.5 mm, or about one-half the pitch in microplate 200. This pitch corresponds to a density of wells of about four wells per 81 mm$^2$. In microplate 300, reference fiducial 306 is positioned about midway between two rows of sample wells along the X direction; in contrast, in microplate 200, reference fiducial 206 is positioned about in line with a row of sample wells along the X direction. This is because the reference fiducials are positioned in approximately the same position in each microplate, but the center line of one row of sample wells in microplate 200 because the center line between two rows of sample wells in microplate 300 as the density of wells is quadrupled.

Sample wells 304 in microplate 300 are similar to sample wells 204 in microplate 200. Sample wells 304 may be characterized by a top diameter $D_{T,384}$, a bottom diameter $D_{B,384}$, a height $H_{384}$, and a cone angle $\theta_{384}$. The preferred values of $D_{B,384}$ and $\theta_{384}$ for microplate 300 are substantially similar to the preferred values of $D_{B,96}$ and $\theta_{96}$ for microplate 200. However, the preferred value for $D_{T,384}$, which is about 4.7 mm, is smaller than the preferred value for $DT_{384}$, which is about 6.7 mm. In microplate 300, the upper diameter must be smaller than the upper diameter of the sample wells in microplate 200, because the sample wells are close packed, leaving no more interwell spacing than necessary for moldability. In turn, the preferred value for $H_{384}$ is about 4.7 mm, so that the wells are elevated by about 7.3 mm. Sample well 304 has a total volume of about 25 μL, and a smallest practical working volume of about 1–12 μL.

Reference fiducial 306 in microplate 300 is essentially identical to reference fiducial 206 in microplate 200.

C. 1536-Well Microplates

FIGS. 17–21 are views of a 1536-well microplate 350 constructed in accordance with the invention. Microplate 350 is similar to microplates 200 and 300, and includes a frame 352 and a plurality of sample wells 354 disposed in the frame. The pitch in microplate 350 is about 2.25 mm, or about one-half the pitch in microplate 300 and about one-fourth the pitch in microplate 200. This pitch corresponds to a density of wells of about sixteen wells per 81 mm$^2$.

Sample wells 354 may be of exclusively frusto-conical shape, like sample wells 204 in microplate 200 and sample wells 304 in microplate 300. However, the volume of such wells would have to be small, about 1–2 μL, due to spatial constraints. Alternatively, sample wells 354 may have a frusto-conical lower portion 306 coupled to a cylindrical upper portion 308. The volume of such wells may be larger, for example, about 7–8 μL. The larger wells permit use of both smaller and larger sample volumes. Larger volumes may be useful if the microplate is used in conjunction with standard fluid dispensing equipment, or if reagents are to be added to the well from stock solutions, such as 100× DMSO or DMF stock solutions.

Reference fiducials in microplate 350 may be essentially identical to reference fiducials 206 in microplate 200 and reference fiducials 306 in microplate 300.

D. Families of Microplates

Together, microplate 200 in FIGS. 9–12, microplate 300 in FIGS. 13–16, and to microplate 350 in FIGS. 17–21 form a set of microplates in which the shape and/or size of sample wells in each microplate is similar, but in which the density of sample wells in each microplate is dissimilar. In particular, each microplate includes a frusto-conical portion characterized by similar cone angles, and microplates 200 and 300 each have similar bottom diameters. Such a set permits a choice of microplate based on the number of samples to be analyzed, where the shape of the sample wells in each microplate is the same, so that the shape may be optimized for dispensing sample to the microplate and/or for conforming to the sensed volume of an optical device, as described below.

E. Application of Sensed Volumes

Figure 22:
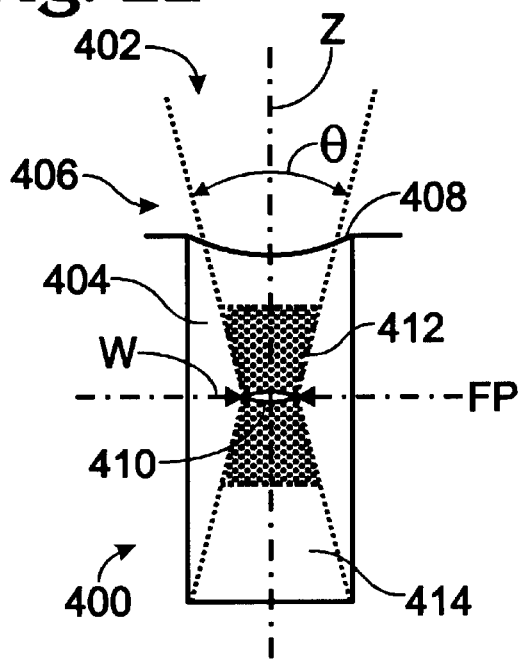
FIG. 22 is a partially schematic cross-sectional view of a standard microplate well.

FIG. 22 is an enlarged cross-sectional view of a standard cylindrical or square microplate well 400, showing air 402 above the sample well, a sample 404 within the sample well, and a light beam 406 passing through the sample well. The interface between air 402 and sample 404 is termed a meniscus 408 and may be convex, plan, or concave.

Light beam 406 is created by an optical device, such as luminescence apparatus 90 described above. The optical device focuses the light so that the light beam has an hourglass shape along a cone or optical axis Z. Light beam 406 is narrowest at its "waist" 410, which has a diameter W and which is located in a focal plane FP of the optical device. Light beam 406 increases in width monotonically above and below waist 410, having a total included angle θ. Angle θ is the cone angle of the "maximum cone" defined by the "marginal rays" of the optical device, and is twice the angle between the marginal rays and the optical axis Z. The marginal rays trace the path of the most outlying light rays normally detectable by the system. The maximum cone defines the outer boundary of the hourglass-shaped light beam and is the volume into which light may be delivered and from which light may be transmitted by the optical device. Angle θ also is the angle subtended at focal plane FP by the light-gathering components (e.g., the objective lens) of the optical device.

Values of W and θ depend on components and properties of the optical device and may be varied by varying these components. For example, cone angle θ is given by the formula θ=2arcsin(NA/n), where "NA" is the numerical aperture of the optical device, and "n" is the index of refraction of the medium adjacent the optical device. Generally, the numerical aperture lies in the range 0.07–1.4, with a preferred range of 0.1 to 0.5 and a preferred value of NA=0.22, corresponding to the numerical aperture of a low-luminescence fused-silica fiber optic cable. The value NA=0.22 is a good compromise, creating a sensed volume that fits into sample wells in a 384-well microplate without hitting walls, and creating a sensed volume that can read to the bottom of microplates conforming to Society of Biomolecular Screening size standards. Generally, the index of refraction lies in the range 1.0–1.6, with a preferred value of n=1.0 corresponding to the index of refraction of air. The preferred numerical aperture and preferred index of refraction correspond to a cone angle of about 25.4°.

The portion of the hourglass to which light may be delivered and from which light may be transmitted further may be limited by one or more confocal optics elements within the optical device. Such confocal optics elements may include apertures placed in image planes of the optical device, conjugate to focal plane FP.

The maximum cone and the confocal optics elements combine to create a sensed volume 412. The shape of sensed volume 412, indicated in FIG. 22 by stippling, may differ in directions parallel and perpendicular to the optical axis Z. Parallel to optical axis Z, the shape may be a Lorentzian, among others. Perpendicular to optical axis Z, the shape may be a Gaussian, or it may be a rounded pulse function, among others. A laser beam might give rise to a Gaussian, whereas a fiber optic bundle might give rise to a rounded pulse function. Generally, lower numerical apertures will create sensed volumes shaped more like cylinders, whereas higher numerical apertures will create sensed volumes shaped more like hourglasses.

Outside the hourglass-shaped beam and sensed volume 412 are optically inaccessible regions 414, from which luminescence is neither excited nor detected. Sample in these regions effectively is wasted, because it does not contribute to the signal. To reduce such waste, the shape and volume of the sample holder may be chosen or designed to conform to the shape and volume of the sensed volume.

Figure 23:
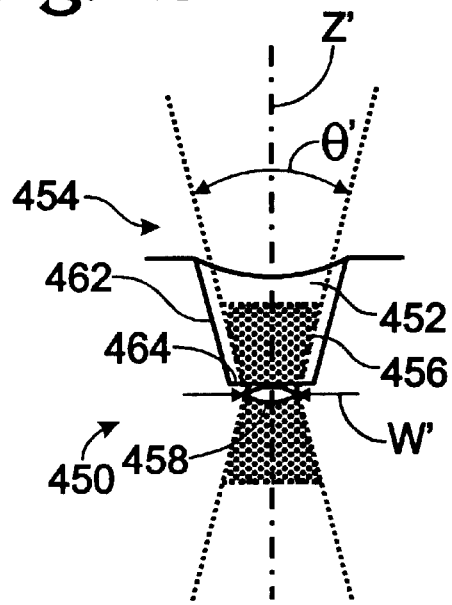
FIG. 23 is a partially schematic cross-sectional view of a sample holder constructed in accordance with the invention.

FIG. 23 is a partially schematic cross-sectional view of a sample holder 450 constructed in accordance with the invention. Sample holder 450 supports a sample 452 illuminated by a light beam 454 forming a sensed volume 456. Sensed volume 456 is shaped substantially like an hourglass, having a waist 458 with diameter W' and conical margins 460 characterized by a cone angle θ' and a cone or optical axis Z'.

Sample holder 450 is configured to support sample 452 so that the shape of the sample conforms to the shape of at least a portion of sensed volume 456. Light is delivered to a sensed volume of the sample from a light source, and transmitted from a sensed volume to a detector. Here, sample holder 450 has a frusto-conical shape configured to conform to substantially one-half of the hourglass shape of sensed volume 456. Specifically, sample holder 450 has conical wall portions 462 that substantially conform to conical margins 460 of sensed volume 456, and a planar bottom portion 464 that substantially conforms to waist 458 of sensed volume 456. For example, the cone angle associated with conical margins 462 substantially equals cone angle θ' of sensed volume 456. In other embodiments, the sample holder may have a purely conical shape or an hourglass shape, so that it conforms to a larger portion of the sensed volume. In yet other embodiments, the sample holder may have yet other shapes, to conform to alternatively shape sensed volumes. Optically inaccessible regions within sample holder 450 are reduced, so that most of the sample contributes to the analysis, reducing sample waste.

Figure 24:
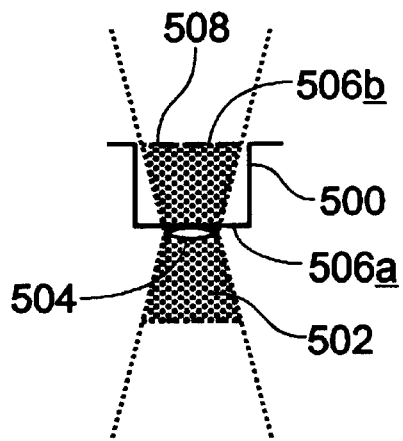
FIG. 24 is a partially schematic cross-sectional view of an alternative sample holder constructed in accordance with the invention.
Figure 25:
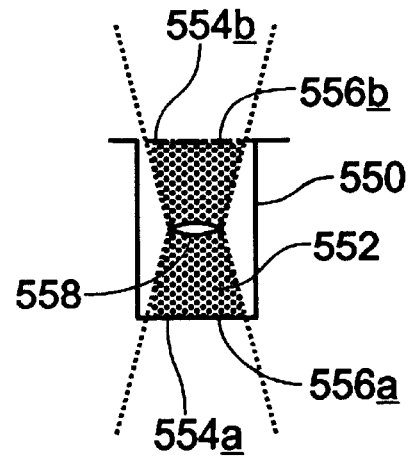
FIG. 25 is a partially schematic cross-sectional view of another alternative sample holder constructed in accordance with the invention.

FIGS. 24 and 25 are partially schematic cross-sectional views of alternative sample holders constructed in accordance with the invention.

FIG. 24 shows a sample holder 500 configured to match substantially half of an hourglass-shaped sensed volume 502. Sample holder 500 is dimensioned so that the waist 504 of the sensed volume may be aligned with the bottom 506a of the sample holder, with the top 508 of the sensed volume substantially aligned with the top 506b of the sample holder. This embodiment may be especially useful for very small sample volumes, such as may be used in 1536-well microplates, because it may increase the sample volume to an amount that may be handled and dispensed more easily.

FIG. 25 shows a sample holder 550 configured to match substantially all of an hourglass-shaped sensed volume 552. Sample holder 550 is dimensioned so that the bottom and top 554a,b of the sensed volume may be aligned with the bottom and top 556a,b of the sample holder, with the waist 558 of the sensed volume substantially in between. This embodiment also may be especially useful for very small sample volumes.

Preferred sample wells are chosen to optimize lower detection limit, signal-to-noise ratio, and signal-to-background ratio, and to minimize sample volume, for a given sensed volume. Lower detection limit is the lowest concentration of sample that can be measured. Signal-to-noise ratio is the signal from the sample divided by variations in the signal due to noise. Signal-to-background ratio is the signal from the sample divided by the signal from contaminants in the sample, the sample holder, and components of the optical system.

Figure 26:
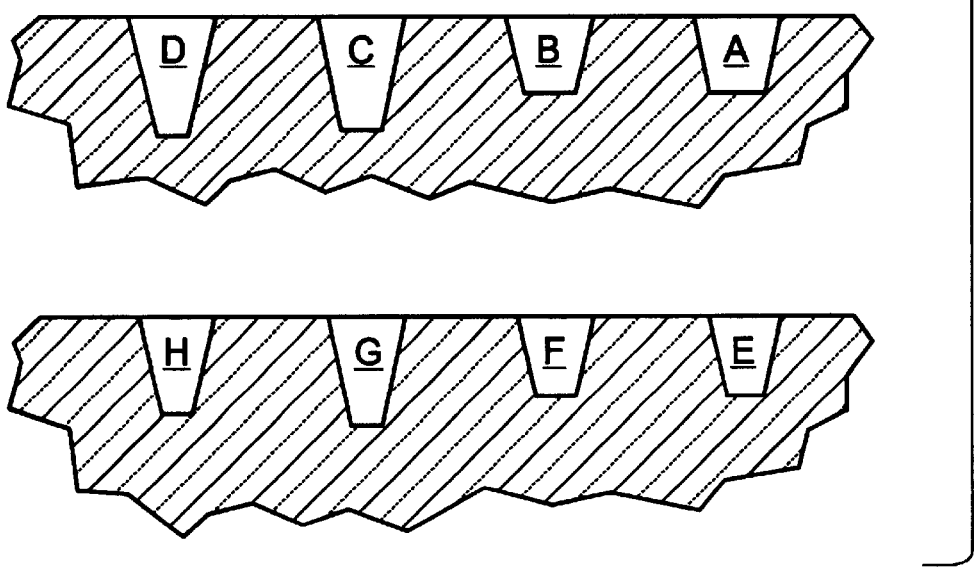
FIG. 26 is a partially schematic cross-sectional view of eight alternative sample holders constructed in accordance with the invention.

FIG. 26 shows eight alternative sample holders constructed to match substantially half of an hourglass-shaped sensed volume. Each well is frusto-conical, but each well differs in its combination of cone angle, well bottom diameter, height, and/or total volume, as summarized in the following table.

| Well Type | Angle (Degrees) | Well Bottom Diameter (mm) | Height (mm) | Total Volume (µL) |
|---|---|---|---|---|
| A | 25.4 | 2.40 | 4.00 | 35.09 |
| B | 20.0 | 2.60 | 4.00 | 34.84 |
| C | 20.0 | 2.00 | 5.70 | 41.93 |
| D | 25.4 | 1.50 | 6.00 | 41.21 |
| E | 26.0 | 1.75 | 4.00 | 23.35 |
| F | 25.4 | 1.75 | 4.00 | 22.94 |
| G | 26.0 | 1.50 | 5.00 | 29.41 |
| H | 25.4 | 1.50 | 4.50 | 23.55 |

Figure 27:
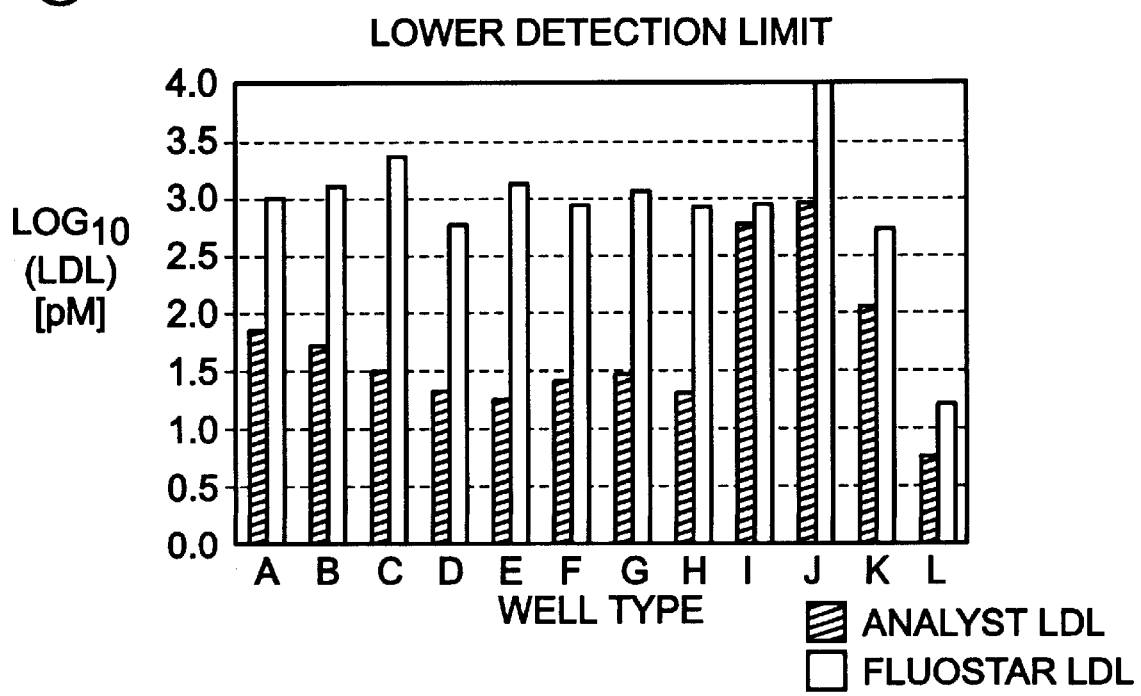
FIG. 27 is a bar graph showing lower detection limits for various sample wells.

FIG. 27 shows lower detection limits for twelve different sample wells. Sample wells A-H correspond to sample wells A–H described above, loaded with 10 µL of sample. Sample wells I–L are standard straight-walled sample wells; sample wells I–K are loaded with 10 µL of sample, and sample well L is loaded with 200 µL of sample. Sample well I is from a COSTAR 384-well microplate, sample wells J and L are from a COSTAR 96-well microplate, and sample well K is from a ROBBINS LV 96-well microplate. Data were collected using two commercial optical devices: (1) an ANALYST high-throughput screening detection platform, marketed by LJL BioSystems, Inc., and (2) a FLUOSTAR system, marketed by BMG Lab Technologies. The ANALYST produces an hourglass-shaped sensed volume similar to that shown in FIG. 4. The displayed value for well J was capped at 4.0; the measured value was 6.29. Optimal results (the lowest detection limit) among sample wells A–H were obtained for sample well H. Optimal results among sample wells I–L were obtained for sample well L (holding 200 µL of sample), which gave slightly better results than sample well H at the expense of using twenty times more sample.

Figure 28:
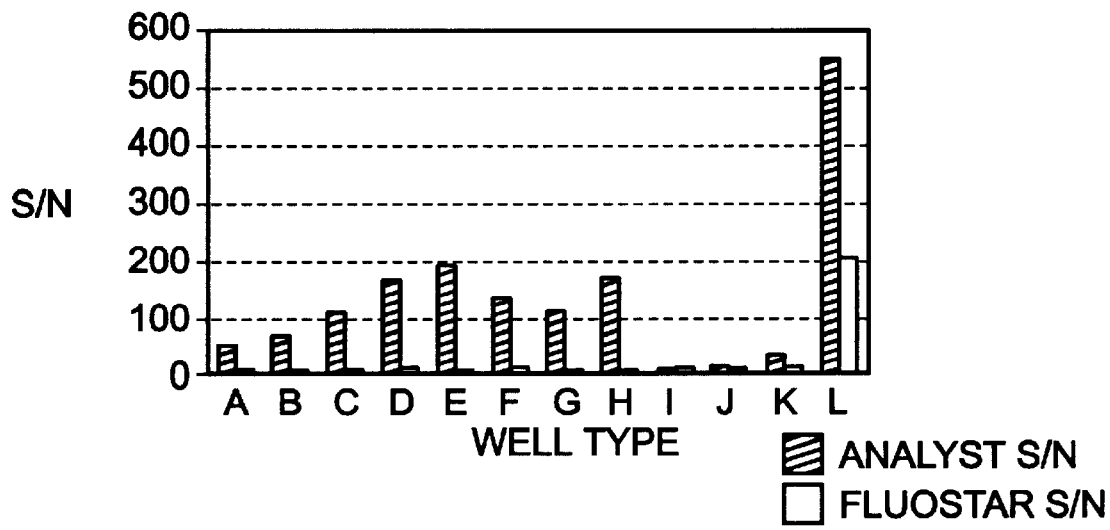
FIG. 28 is a bar graph showing signal-to-noise ratios for the sample wells of FIG. 27.

FIG. 28 shows signal-to-noise ratios obtained for the optical devices and sample wells used in FIG. 27. Optimal results (the highest signal-to-noise ratios) among sample wells A–H were obtained for sample wells D, E, and H. Optimal results among sample wells I–L were obtained for sample well L.

Figure 29:
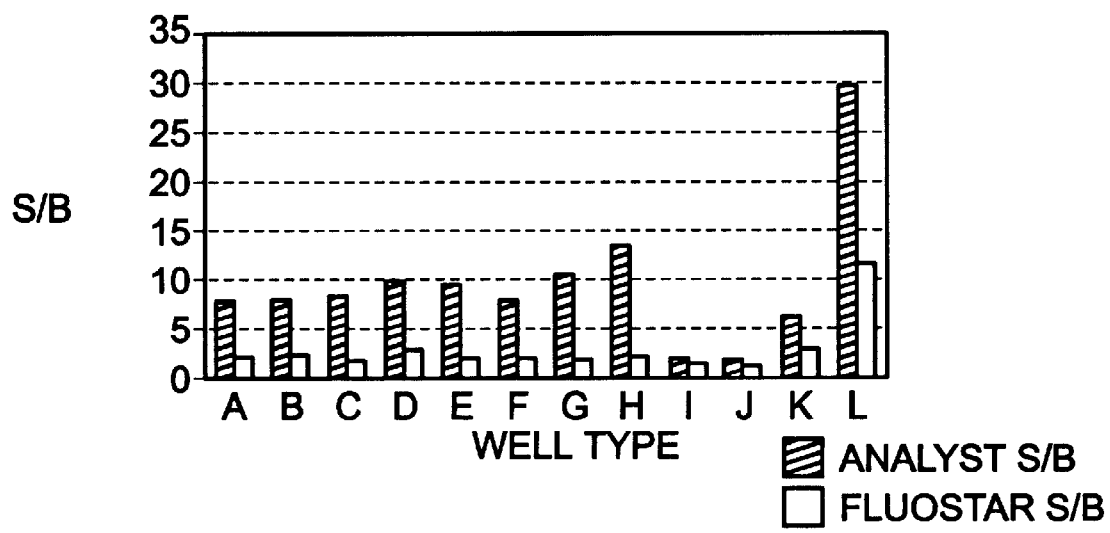
FIG. 29 is a bar graph showing signal-to-background ratios for the sample wells of FIG. 27.

FIG. 29 shows signal-to-background ratios obtained for the optical devices and sample wells used in FIG. 27. Optimal results (the highest signal-to-background ratios) among sample wells A–H were obtained for sample well H. Optimal results among sample wells I–L were obtained for sample well L.

Importantly, sample wells A–H significantly outperformed sample wells I–K with regard to lower detection limit, signal-to-noise ratio, and signal-to-background ratio, especially when used with the ANALYST detection platform, which forms a sensed volume. Thus, for a given volume of fluid, the frusto-conical sample wells outperform the straight-walled sample wells. In fact, the performance differences shown may understate actual performance differences, because data for wells A–H were collected from machined DELRIN prototypes rather than molded prototypes. Machined prototypes generally are associated with lower signal-to-noise and signal-to-background ratios than molded prototypes, due to scattering and other factors.

Sample wells A–H (especially sample well H) are similar to sample wells 204 and 304 in microplates 200 and 300, as described above. In these wells, the cone angle of the sample holder substantially conforms to the approximately 25° cone angle of the sensed volume of the ANALYST optical device. For frusto-conical wells, optimal cone angles and well bottom diameters will depend on the cone angle and waist diameter of the sensed volume. Cone angles may range from about 8° for a low (0.07) NA optical system, on up. Such cone angles significantly exceed the slight 1–2° angle introduced into molded cylindrical sample holders to permit removal of the sample holder from the molding tool. Bottom diameters may range from about 1 $\mu$m for a high NA optical system, on up, though typical values might be 1 mm or 1.5 mm.

The smallest practical working volume for frusto-conical and other sample holders is the volume for which there still is sufficient sample volume to enclose the portion of the sensed volume contained within the sample well, or at least to enclose a sufficient portion of the sensed volume to yield acceptable signal-to-noise and signal-to-background ratios.

If the apparatus is sufficiently flexible, the shape and volume of the sensed volume produced by the apparatus may be adapted like a probe to match the shape and volume of the sample holder. In this way, the sensed volume may be expanded for maximum signal in a large sample holder, and contracted to avoid nearby walls in a small sample holder.

Alternatively, the shape and volume of the sensed volume may be held constant, and the position of the sensed volume varied to match the sample holder and/or assay. In this way, the sensed volume will report on equal volumes of each composition analyzed, so that the apparatus effectively reports "intensive" quantities. Intensive quantities do not depend on the amount of composition in a sample holder; in contrast, extensive quantities do depend on the amount of composition in the sample holder. This approach can be used to facilitate comparison of results obtained from different-sized sample wells. This approach also can be used to facilitate comparison of results obtained from like-sized sample wells containing different volumes of solution.

F. Factors Affecting Sensed Volume

Figure 30:
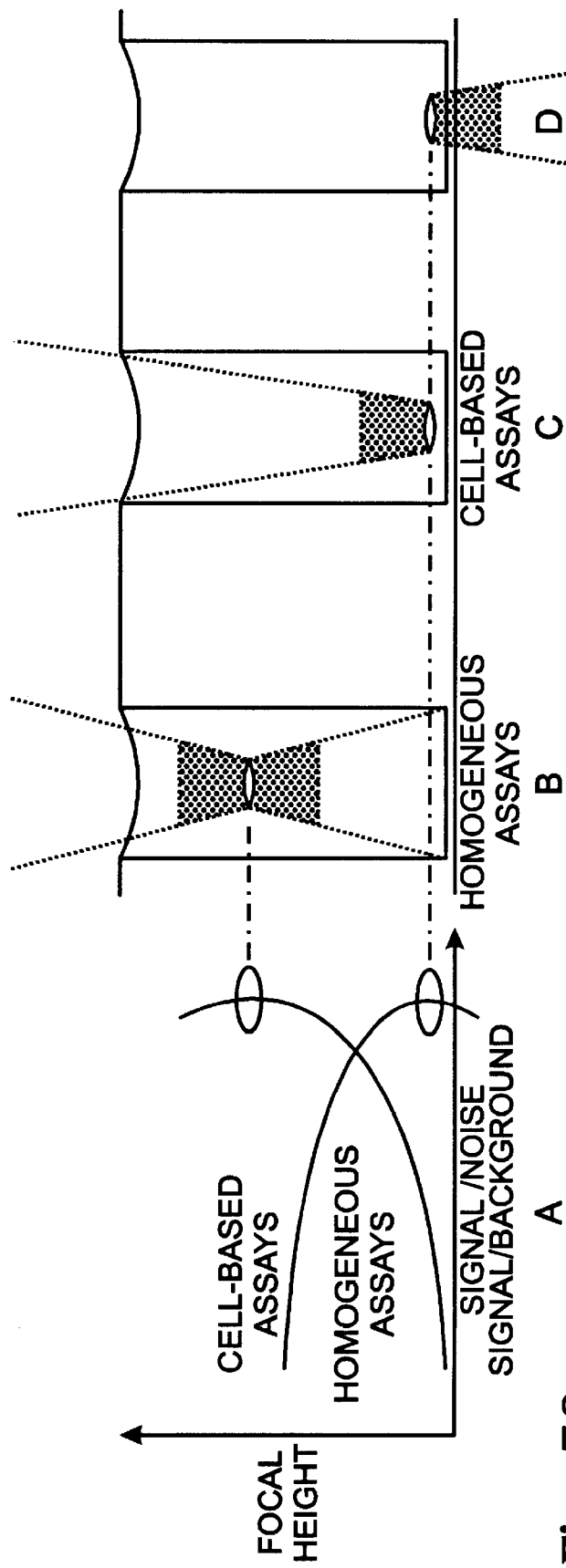
FIG. 30 is a partially schematic cross-sectional view of three sample wells, showing alternative positions of a sensed volume.

FIG. 30 shows how the sensed volume can be directed to different regions of a standard microplate well, and how directing the sensed volume affects signal-to-noise and signal-to-background ratios.

In homogeneous assays (Panel B), photoluminescent molecules are distributed uniformly throughout the composition, and the optimum signal-to-noise and signal-to-background ratios are obtained regardless of well geometry when the sensed volume is positioned in the middle of the composition (Panel A), so that the sensed volume does not overlap with the meniscus or the bottom or sides of the well. If the meniscus is in the sensed volume, light reflected from the meniscus will be detected. This will decrease sensitivity by increasing background and decreasing signal. If the bottom of the well is in the sensed volume, light reflected from the well bottom will be detected. Moreover, noncomposition photoluminescence arising from fluorescent and other photoluminescent materials that are commonly included in the microplate or adsorbed to the walls of the microplate also will be detected. These two effects will decrease sensitivity by increasing background and decreasing signal. Luminescence measured from the microplate walls will lead to spuriously high luminescence intensities and luminescence polarizations.

In cell-based assays (Panels C and D), photoluminescent molecules are concentrated in or near cells growing at the bottom of the well, and the optimum signal-to-noise and signal-to-background ratios are obtained when the sensed-volume is centered about the bottom of the well (Panel A). Such centering may be accomplished either using top optics (Panel C) or bottom optics (Panel D).

For some cell-based assays, microplate wells having a frusto-conically-shaped portion may be particularly advantageous. The conical shape of the well tends to focus cells into a smaller area defined by the substantially flat bottom wall. The conical shape of the well and the selected confocal optics allow substantially all of the cells at the bottom of the well to be detected in the sensed volume, thus maximizing signal sensitivity and reagent utilization regardless of whether the cells are uniformly distributed across the bottom of the well. The conical geometry of the wells also makes it possible to perform cell-based assays from the top without requiring transmission of light through the bottom wall of the well. The geometry is also useful for performing fluorescence polarization assays which may be based on receptor/ligand binding to the bottom of the well.

The shape and position of the sensed volume within the well may be affected by (1) the meniscus and (2) the geometry of the sample well, among other factors.

Figure 31:
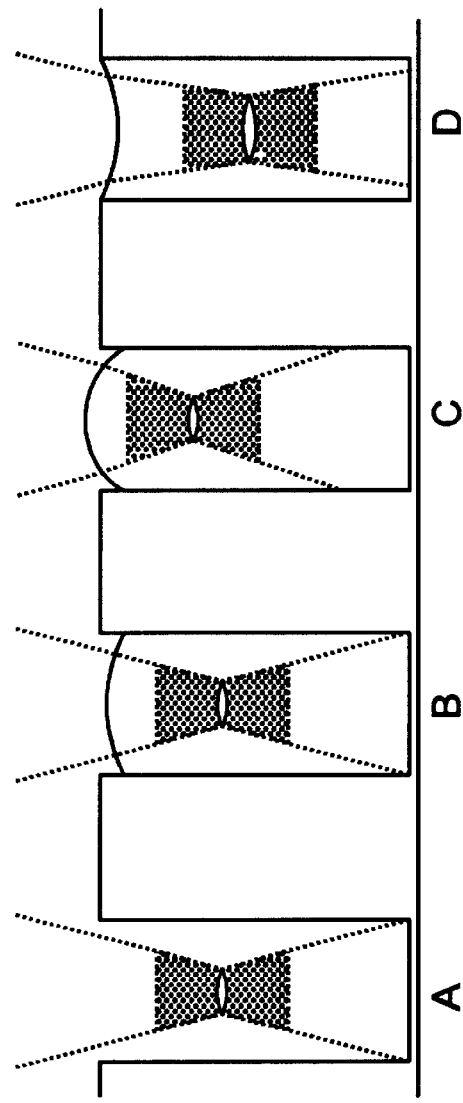
FIG. 31 is a partially schematic cross-sectional view of four sample wells, showing how the meniscus affects the shape and position of the sensed volume within a sample well.

FIG. 31 shows how the meniscus affects the shape and position of the sensed volume within a sample well. The meniscus affects the sensed volume because light is refracted as it crosses the meniscus boundary between the air and the composition. Specifically, light passing from air (with its lower index of refraction) into the sample (with its higher index of refraction) bends toward the normal, as described by Snell's law. Here, the normal is the direction perpendicular to the surface of the meniscus at a given point. If there is no fluid and hence no meniscus, the beam has a nominal undistorted shape (Panel A). If the meniscus is everywhere perpendicular to the light beam, then light passing through the meniscus will not bend, and the beam will retain its nominal undistorted shape (Panel B). For a converging beam, this will occur when the meniscus is appropriately convex. If the meniscus is more than appropriately convex, light will bend toward the middle of the well as it passes through the meniscus, and the sensed volume will be compressed and raised (Panel C). If the meniscus is less than appropriately convex, flat, or concave, light will bend away from the middle of the well as it passes through the meniscus, and the sensed volume will be stretched and lowered (Panel D).

Sample wells can be configured to account for these changes in the shape and position of the sensed volume created as excitation and emission light passes through the meniscus. The invention includes shaping the sample well to account for changes in the shape and position of the sensed volume, and shaping and treating the sample well to alter the shape of the meniscus, as appropriate.

Figure 32:
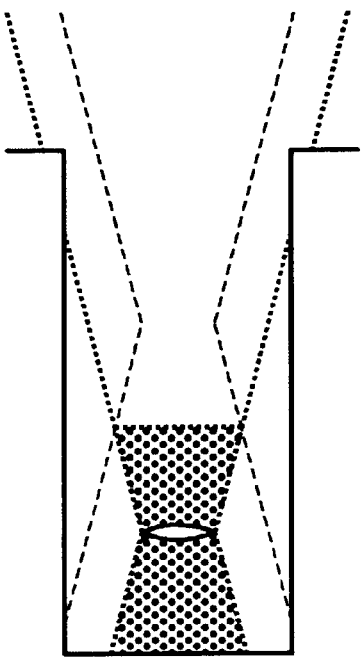
FIG. 32 is a partially schematic cross-sectional view of a sample well, showing how the geometry of the sample well affects the position of the sensed volume.
Figure 33:
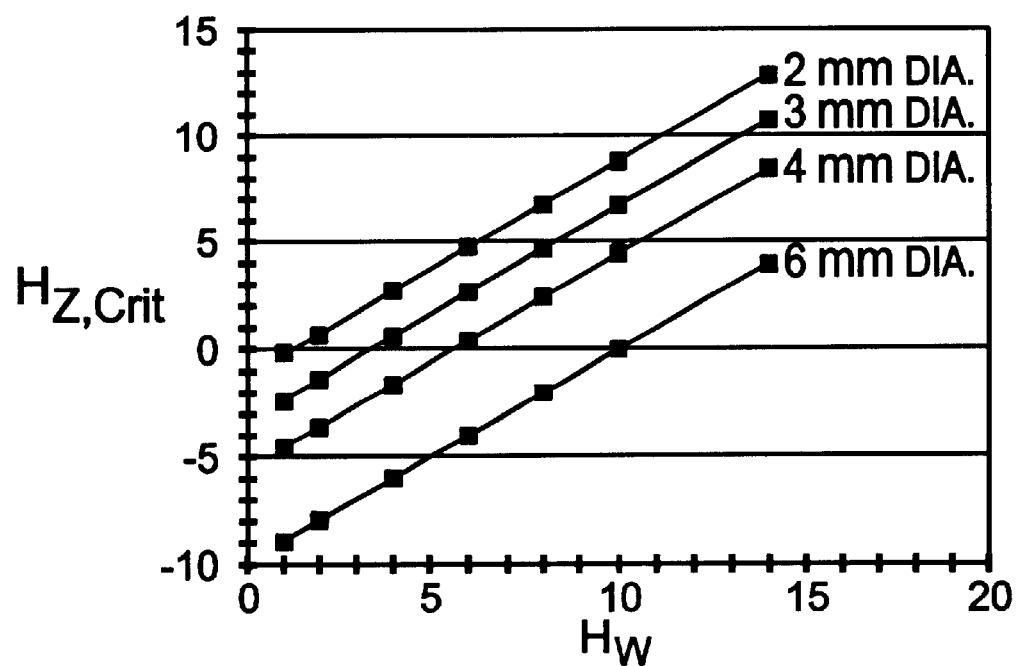
FIG. 33 is a graph showing the relationships between critical Z-height and microplate well height.

FIGS. 32 and 33 show how the geometry of the sample well affects the position of the sensed volume. In particular, if the well is sufficiently narrow relative to the diameter of the beam, or if the well is sufficiently deep relative to the angle made by the beam, then the light beam may impinge upon the top walls of the well. In these cases, setting the Z-height too low can reduce sensitivity (1) by decreasing the desired signal because less light enters the well, and (2) by increasing the background because the light beam illuminates the tops of wells. Many microplates are made from materials that are fluorescent or otherwise photoluminescent, and the instrument will detect this photoluminescence from materials at the tops of wells.

Because beam position is a critical determinant of signal to noise, Z height must be appropriately maintained; Z height should be kept above a critical focal height, $H_{Z,Crit}$. The height at which the beam first impinges on the walls of the well is the critical focal height, $H_{Z,Crit}$. FIG. 33 shows how $H_{Z,Crit}$ depends on the well height $H_W$ and well diameter $D_W$, for a beam of diameter 1.5 millimeters (mm) and a beam angle 25.4°. Similarly, Table 1 shows how $H_{Z,Crit}$ depends on well height and well diameter for four commercially available microplates.

| Plate Type | Well Height (mm) | Well Diameter (mm) | $H_{Z,Crit}$ (mm) |
|---|---|---|---|
| Costar Black Flat Bottom 96-Well 3915 | 10.71 | 6.71 | −0.85 |
| Dynatech MicroFluor Round Bottom | 9.99 | 6.78 | −1.72 |
| Costar Black 384-Well 3710 | 11.55 | 3.66 | 6.76 |
| Packard White 384-Well #6005214 | 11.57 | 3.71 | 6.67 |

The increase in $H_{Z,crit}$, shows that for a microplate having a standard height and XY area, as the aspect ratio (length/diameter) and density of wells increases, the ability of a confocal optic system to read small volumes in standard straight-walled wells decreases. This may require reading through the bottom of the well for cell-based assays, which is not always convenient or practical.

Z-height can be optimized for a particular microplate and assay by (1) preparing a test microplate with representative assay (e.g., blanks, positive and negative controls, dilution series), (2) and reading the microplate multiple times at different Z-heights to determine the Z-height that gives the best signal-to-background data. Some combinations of assay and microplate are relatively insensitive to Z-height, while others demonstrate a distinct optimum.

A sample holder sensor switch may be mounted on the top optics head of luminescence apparatus 90 to prevent the microplate from contacting the optics head in case the microplate is misaligned, not properly specified, or the Z-height is set incorrectly. If this sensor switch detects a fault, the sample holder may be ejected prior to reading.

G. Reference Fiducials

Microplates and biochips are of demonstrated utility in automated screening; however, they suffer from a number of shortcomings. Some shortcomings result from variations within the microplate and biochip. For example, microplates and biochips typically are made of plastic and may suffer distortions in the positions of sample wells and features due to shrinkage or expansion of the plastic. Other shortcomings result from inherent inaccuracies in the alignment mechanisms used to position microplates and biochips for sample analysis. Yet other shortcomings result from holder-to-holder variations in the microplate and biochip. For example, the overall size, sample well or feature size, construction material, and sample well or feature number and arrangement may vary. To circumvent holder-to-holder variations, devices may limit sample analysis to only a single type of sample holder, such as a 96-well microplate.

If the positional error due to plastic deformation, inaccurate alignment mechanisms, or holder-to-holder variations in sample holders is a significant fraction of the feature size, then sample analysis will be adversely affected. For example, fluorescence signals may be decreased, and crosstalk from adjacent sites may be increased, especially when the array of sample wells or features is read with a step-and-repeat optical reader, which relies on moving to predetermined locations to perform fluorescence intensity measurements. These problems will be particular severe as the sample wells and features become smaller.

Reference fiducials are reference features used to provide information that facilitates sample handling and/or analysis. Typically, the reference fiducial is configured to be interpretable by the same detection system that detects light transmitted from the sample. The reference fiducial may be configured to provide a variety of information. For example, the reference fiducial may encode information regarding microplate layout, including the dimensions of the sample wells alone, and the dimensions, composition, and manufacturer of the microplate as a whole. Such information may be used to reduce cross-plate drift and/or to facilitate alignment of the sample holder and a detection system and/or fluid dispensing system, among other applications. Such information also may be used to set up the instrument for a particular preselected assay, if the information is determined before the assay.

Reference fiducials also may be configured to provide information regarding background luminescence. For example, if a reference fiducial includes an aperture through the frame, information regarding background may be obtained by scanning the aperture and a portion of the frame adjacent the aperture with the detection system to determine their luminescence, and then comparing the luminescence of the aperture with the luminescence of the portion of the frame adjacent the aperture.

Figure 34:
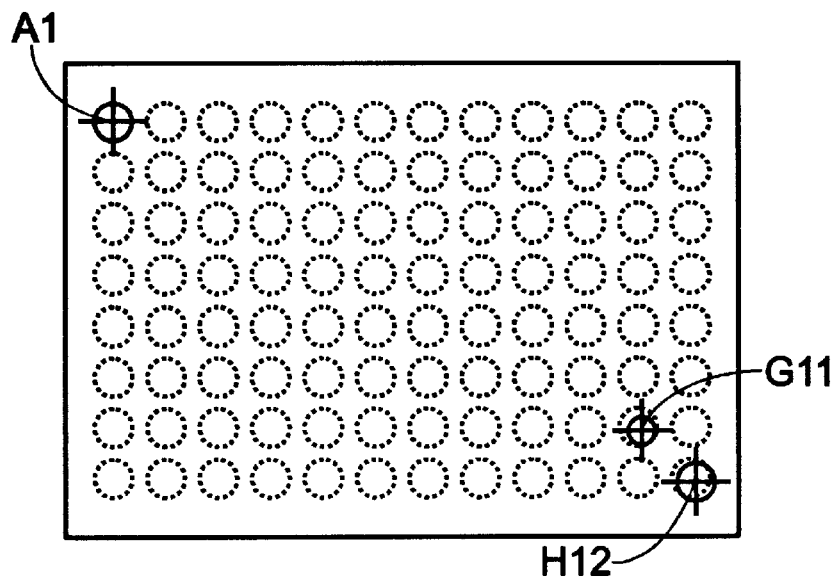
FIG. 34 is a schematic top view of a microplate showing the effects of cross-plate drift.

FIG. 34 shows a schematic top view of a 96-well microplate, showing how the geometry of the microplate affects the position of the sensed volume. A microplate apparatus may be configured automatically to find the location of each sample well in a given microplate, beginning with sample well A1. The apparatus may do this using stored parameters that describe the dimensions (e.g., microplate heights, interwell distances, etc.) of the particular microplate style. However, these microplate parameters are nominal and do not account for unit-to-unit or lot-to-lot variations in microplate geometry. If there is a slight variation in interwell distance, a calculated position may be off-center on some sample wells, even though it is perfectly on-center on sample well A1. This effect is termed cross-plate drift.

Cross-plate drift of fluorescence readings may increase as the instrument scans across the microplate, because variations will be compounded. Typically, drift will be worst at well H12, which is farthest from well A1. Such drift can be reduced by making the stage more accurate, by making the size of the sample holders more consistent, or by adjusting the apparatus to reduce the diameter of the observation region, thereby "putting it back" into the sample well. The lattermost approach is shown for well G11, relative to well H12.

Figure 35:
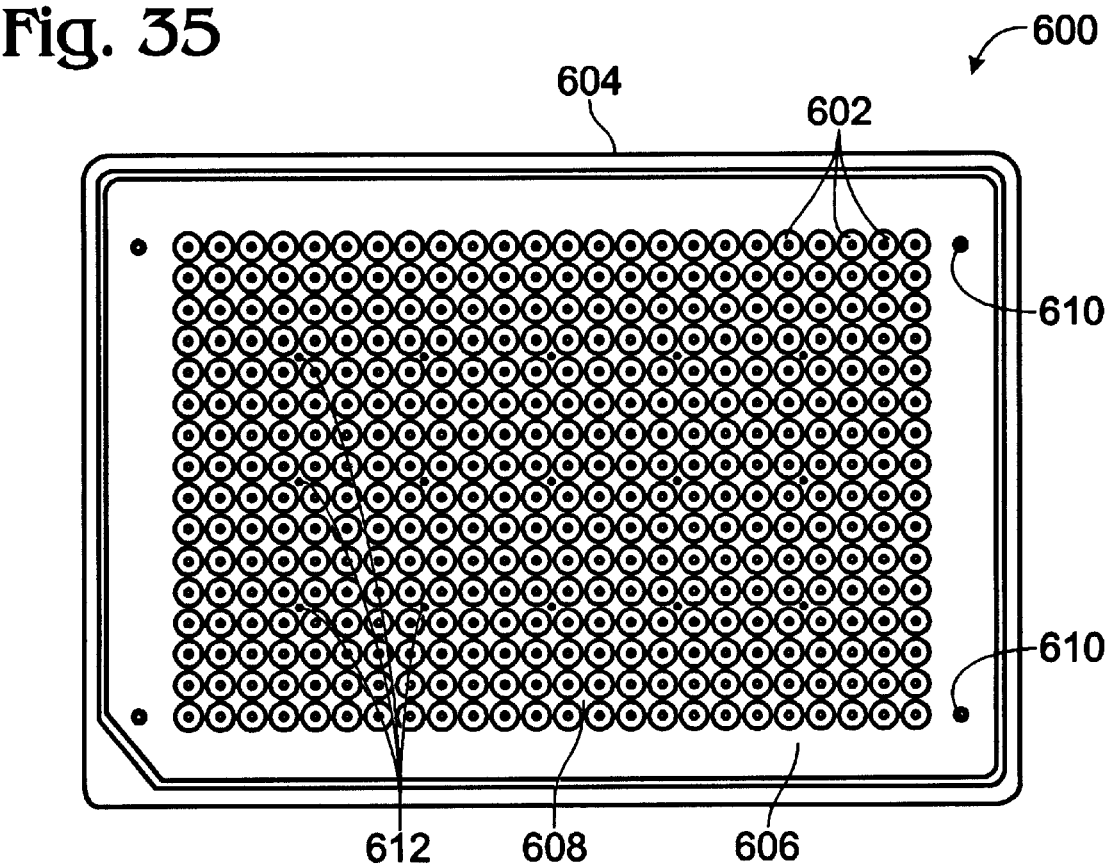
FIG. 35 is a top view of a 384-well microplate having a plurality of reference fiducials.

FIG. 35 shows a top view of a 384-well microplate 600 constructed in accordance with the invention, showing how reference fiducials may be used to reduce cross-plate drift. Microplate 600 includes sample wells 602 and a frame 604 having an edge region 606 and a sample well region 608. Microplate 600 also includes global reference fiducials 610 disposed in edge region 606 and local reference fiducials 612 disposed in sample well region 608.

Global and local reference fiducials may be employed as follows. First, an appropriate detection system locates the global reference fiducials. Second, the detection system locates the local reference fiducials for a given working area (defined as the sample wells adjacent the local reference fiducial), based on the positions of the global reference fiducials. When moving to new working areas, appropriate local reference features are located prior to processing. In principle, utilizing this technique, any desired level of positional accuracy may be obtained if enough reference fiducials are used to compensate for the distortion present in a microplate or biochip substrate.

Figure 36:
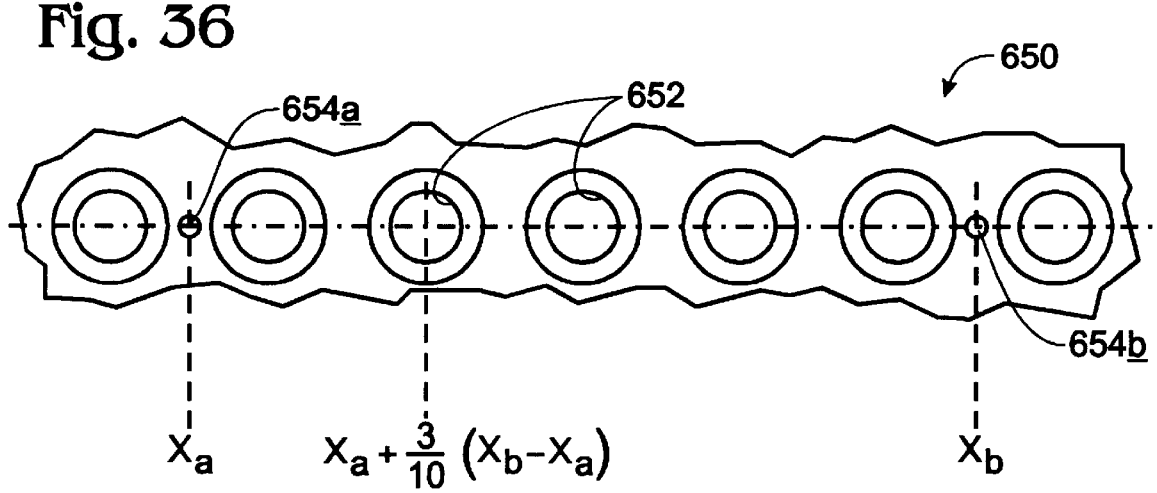
FIG. 36 is a top view of a portion of a microplate having a plurality of reference fiducials.

FIG. 36 shows a portion 650 of a microplate, showing how reference fiducials and an interpolation scheme may be employed to reduce cross-plate drift. Portion 650 includes seven sample wells 652 and two local reference fiducials 654$a,b$. First, the positions $X_a$ and $X_b$ of local reference fiducials 654$a,b$ are determined, a task that may be facilitated using information from any global reference fiducials. Second, the separation X between the two local reference fiducials is determined by subtraction, $X=X_a-X_b$; a generalization of this formula (expressing the distance between two points) may be used for more complicated situations. Third, the separation is divided by five (the number of intervening sample wells). Finally, the position of each sample well is calculated by (1) adding multiples of one-fifth the separation to the position of the reference fiducial corresponding to the number of intervening sample wells and (2) adding an additional offset of one-tenth the separation to the position of the reference fiducial corresponding to the distance from a reference fiducial to the first sample well. Generally, reference fiducials may be used to determine the positions of sample wells and other reference fiducials using a variety of algorithms. These algorithms may involve interpolation, extrapolation, and/or other approaches.

Global and local reference fiducials play complementary roles. Overall variations in the sample holder generally may be determined more accurately using the global reference fiducials than the local reference fiducials, because global reference fiducials generally will be farther apart, so that errors in determining the positions of the reference fiducials will be less significant. Conversely, local variations in the sample holder generally may be determined more accurately using the local reference fiducials, because the relative positions of the global reference fiducials effectively average out local variations.

Reference fiducials may be employed not only to facilitate calculation of the positions of sample wells within the plane of the microplate, but also to facilitate calculation of positions perpendicular to the plane of the microplate. Such calculations allow the detection system to maintain an equal distance from the sample holder, independent of whether the sample holder is locally or globally warped.

Figure 37:
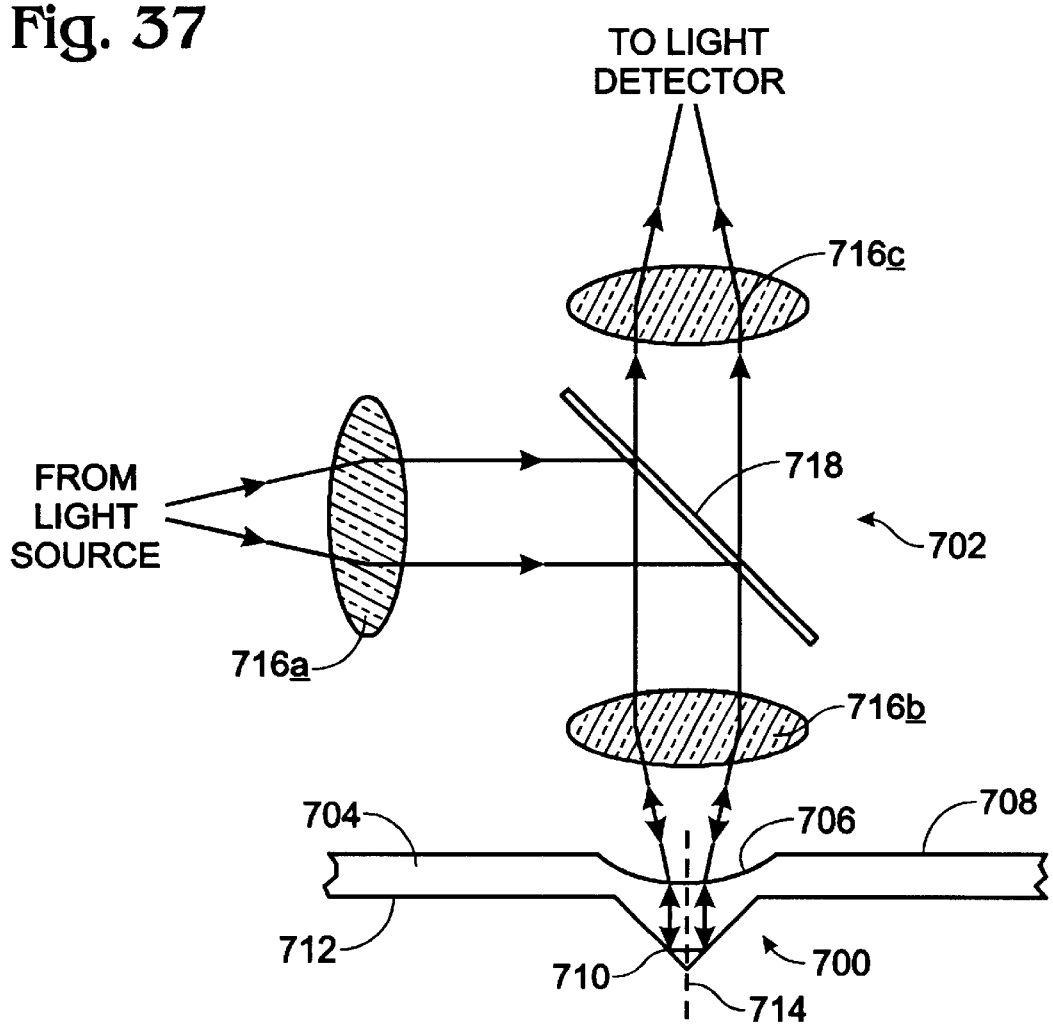
FIG. 37 is a partially schematic side elevation view showing a reflective reference fiducial in use.

FIG. 37 shows a partially schematic side elevation view of a reflective reference fiducial 700 and a detection system 702. Reflective reference fiducial 700 is molded into a microplate 704, and includes (1) a curved surface 706 near the top 708 of the microplate and (2) an angled surface 710 near the bottom 712 of the microplate. Reflective reference fiducial 700 has cylindrical symmetry about an axis 714 connecting curved surface 706 and angled surface 710. Detection system 702 includes (1) a light source, (2) first, second, and third lenses 716$a$–$c$, (3) a beamsplitter 718, and (4) a detector. Detection system 702 may be the same detection system used to detect light transmitted from a sample in microplate 704 during sample analysis.

Reflective reference fiducial 700 acts effectively as a small mirror, reflecting light transmitted by detection system 702 back into the detection system when the detection system and the reference fiducial are appropriately aligned. In this way, information encoded by the reference fiducial may be interpreted by the detection system. In use, light rays (denoted by arrows) from the light source pass through first lens 716$a$ and are reflected off beamsplitter 718 through second lens 716$b$ and onto curved surface 706. Curved surface 706 collimates the light rays and directs the collimated light rays onto angled surface 710. The collimated light rays are totally internally reflected by angled surface 710 and are directed back through second lens 716$b$ beamsplitter 718, and third lens 716$c$ to the detector. Reflective reference fiducials may be formed of the same material used to form the frame and sample wells, deriving their reflective properties in part from total internal reflection; reflective reference fiducial 702 is an example. Reflective reference fiducials also may be formed of different materials, such as silver, deriving their reflective properties all or in part by ordinary reflection; a silvered spherical mirror is an example. The position of reflective reference fiducial 700 may be located in the X and Y directions by scanning detection system 702 over the reference fiducial. Reflective reference fiducial 700 may function as a local and/or global reference fiducial.

Generally, the reference fiducials may include any reference feature associated with a sample holder like a microplate or a biochip that is configured to provide information that facilitates sample handling and/or analysis. The reference fiducial may include (1) an aperture through all or part of the frame, (2) a reflective portion, and/or (3) other optical, acoustical, and/or mechanical features, among others. For example, a mechanical reference fiducial could be read using a linear voltage displacement transducer (LVDT), which measures displacement by creating a voltage proportional to the displacement.

Information may be encoded by the reference fiducial in various ways. Information may be encoded by size, shape, position, color, reflectivity, and/or other means. Information also may be encoded by the relative sizes, shapes, positions, colors, and/or reflectivities of a plurality of reference fiducials. Information also may be encoded by the ability of the reference fiducial to absorb, transmit, or reflect incident light; for example, if the detection system is capable of transmitting light to the reference fiducial.

The invention also provides methods for using reference fiducials. For example, the invention provides a method of reducing cross-plate drift during sample analysis. This method includes (1) providing a sample holder having a frame, a plurality of sample positions disposed in the fame, and at least two positional reference fiducials disposed in the frame, (2) determining the position of the positional reference fiducials, and (3) calculating the positions of the sample positions, based on the positions of the positional reference fiducials and the known relationship between the positions of the sample positions and the positions of the positional reference fiducials. The sample holder may include microplates, biochips, and other sample holders.

Although reference fiducials were described primarily in the context of microplates, they also may be used with other sample holders, such as biochips. Biochips are substantially planar semiconductor devices used to hold and study biomolecules; a familiar example is a gene chip used to hold nucleic acids. Biochips may include many discrete sample positions, like microplates. Indeed, microplates begin to merge with biochips, such that the concept of a sample well begins to merge with the concept of a feature on a biochip, for microplates having very small sample wells.

H. Prevention of Formation and Trapping of Bubbles

Figure 38:
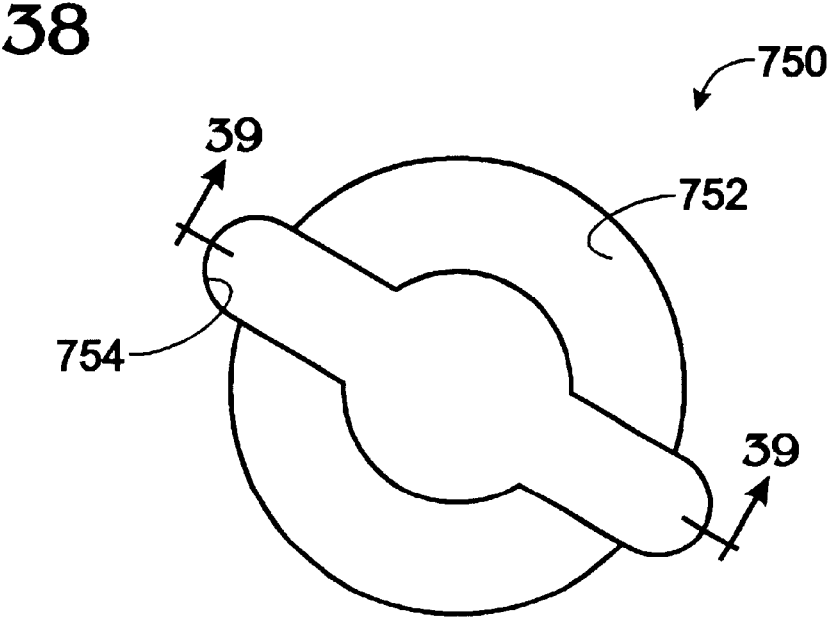
FIG. 38 is top view of a sample holder constructed in accordance with the invention.
Figure 39:
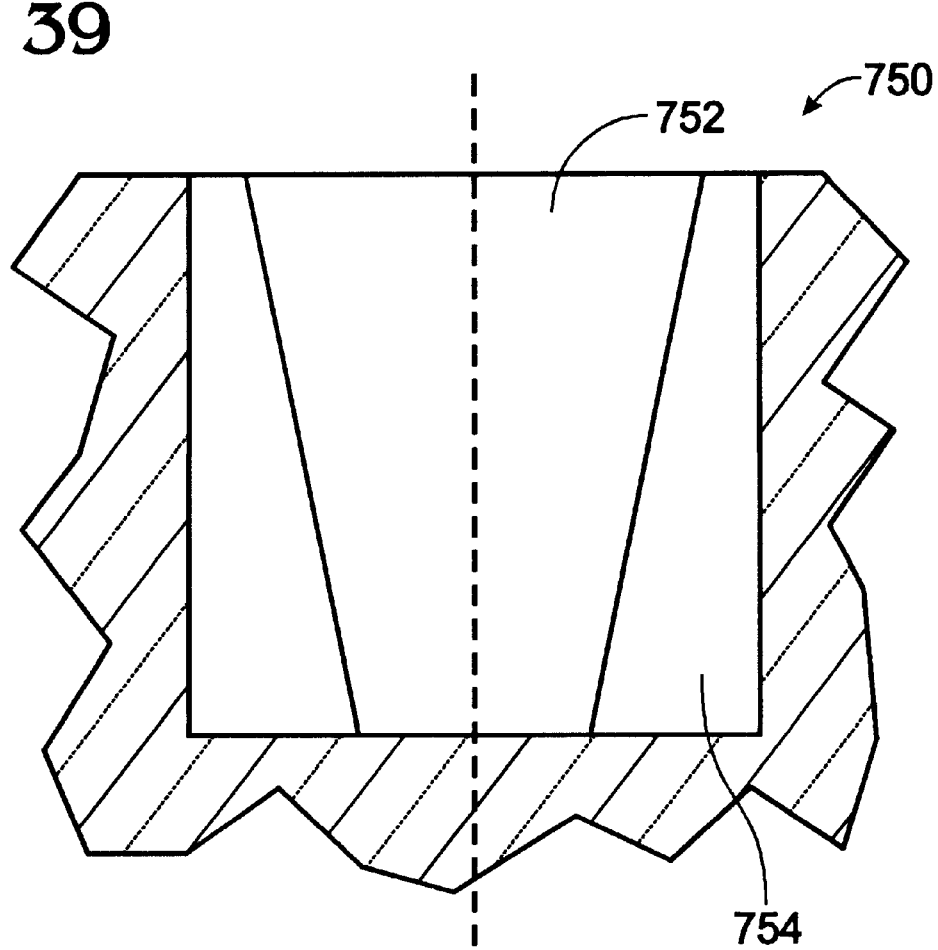
FIG. 39 is a cross-sectional view of the sample holder shown in FIG. 16, taken generally along line 39—39 in FIG. 38.

FIGS. 38 and 39 are views of a sample holder 750 that has been configured to reduce the formation and trapping of bubbles as the sample holder is filled with a fluid sample. Sample holder 750 may be used alone or as part of a microplate or other holder. Sample holder 750 includes a major portion 752 and a minor portion 754. Major portion 752 holds a sample to be analyzed by an optical device. Major portion 752 may have a variety of sizes and shapes; in sample holder 750, major portion 752 has a frusto-conical shape that substantially conforms to an hour-glass shaped sensed volume. Minor portion 754 reduces the formation and trapping of bubbles. Minor portion 754 may have a variety of sizes and shapes; in sample holder 750, minor portion 754 is a channel that permits air to escape from the well during filling.

Sample holders constructed in accordance with the invention also may use other shapes or mechanisms to reduce the formation and trapping of bubbles. Sample holders may be shaped to reduce or eliminate corners and other tight spaces that may trap bubbles. For example, sample wells may have rounded rather than pointed bottoms, because it may be more difficult to displace air from a pointed bottom due to surface tension effects. The curvature of the rounded bottom may be selected based on surface tension in representative samples. Sample holders also may be coated with materials that reduce the affinity of bubbles for the microplate walls.

1. Composition of Microplates

Microplates are preferably made of polystyrene with carbon black at a concentration of 1.5 to 3.0% (w/w). The carbon raw material should be ultra-pure carbon powder of substantially uniform size, and surface area. Various factors are considered to determine the optimum carbon concentration. Increasing carbon concentration may decrease autoluminescence from the polystyrene and also decrease resistivity which reduces static electricity. Static build-up on the plate may cause undesirable effects such as droplet deflection, bubble formation, meniscus effects, attraction of potentially interfering luminescent particles from the air. On the other hand, carbon powder usually contains a small concentration of luminescent particles. Therefore, a relatively high carbon concentration may result in "hot wells."

The plate manufacturing environment should be clean to avoid incorporation of fluorescent contaminants. In the molding process it is important to use optimum temperature and pressure conditions and to control the flow-rate of polymer into the mold so that the mold is filled uniformly. Uniform cooling of the molded material is also important. The finished plate should be handled by a robot or an operator wearing clean "powder-free" gloves. The microplates are then stacked in bags made of non-leaching food grade, polyethylene.

J. Methods

The invention also provides various methods. For example, the invention provides a method of improving signal detection in luminescence assays, which includes (1) selecting an optical device capable of detecting light from a sensed volume, (2) selecting a sample holder having a shape configured to conform to the shape of the sensed volume, and (3) performing a luminescence assay using the optical device and the sample holder. The method further may include aligning the sensed volume with the sample holder.

Although the invention has been disclosed in preferred forms, the specific embodiments thereof as disclosed and illustrated herein are not to be considered in a limiting sense, because numerous variations are possible. For example, although reference fiducials were described primarily in the context of microplates, they also may be used with other sample holders, such as biochips. Applicants regard the subject matter of their invention to include all novel and nonobvious combinations and subcombinations of the various elements, features, functions, and/or properties disclosed herein. No single element, feature, function, or property of the disclosed embodiments is essential. The following claims define certain combinations and subcombinations of elements, features, functions, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of Applicants' invention.

We claim:

1. A system for detecting light transmitted from a sensed volume, the system comprising:

an optical device capable of detecting light substantially exclusively from a sensed volume; and a sample holder configured to support a sample so that the shape of the sample substantially conforms to a conical portion of the sensed volume;

wherein the optical device is configured to direct light through an opening characterized by a numerical aperture; and wherein the cone angle of the conical portion of the sensed volume is determined at least in part by the numerical aperture.

2. The system of claim 1, wherein the sample holder has a frusto-conical shape.

3. The system of claim 1, further comprising at least a second sample holder, wherein the sample holders are disposed as wells in a microplate.

4. The system of claim 3, wherein the number of wells in the microplate is selected from the group consisting of 96, 384, and 1536.

5. The system of claim 3, wherein the wells are organized in a density of at least about 1 well per 81 mm$^2$.

6. The system of claim 1, wherein the sensed volume has a waist.

7. The system of claim 1, wherein the sensed volume has an hourglass shape, and wherein the sample holder has a conical shape configured to conform to substantially one-half of the hourglass shape.

8. The system of claim 1, wherein the sensed volume has an hourglass shape, and wherein the sample holder has a frusto-conical shape configured to conform to substantially one-half of the hourglass shape.

9. The system of claim 8, wherein the conical portion of the frusto-conical shape is characterized by a cone angle of at least about 8°.

10. The system of claim 8, wherein the conical portion of the frusto-conical sample holder is characterized by a cone angle of about 25°.

11. The system of claim 8, the sample holder having a top and a bottom, wherein the diameter of the bottom of the sample holder is about 1.5 millimeters.

12. The system of claim 1, wherein the sensed volume has an hourglass shape, and wherein the sample holder has a cylindrical shape configured to correspond to substantially all of the hourglass shape.

13. The system of claim 1, wherein the optical device includes:
an examination site;
a light source positioned to deliver light to the examination site;
a detector positioned to receive light transmitted from the examination site; and
an optical relay structure capable of transmitting light substantially exclusively from a sensed volume of a sample positioned at the examination site to the detector.

14. The system of claim 1, wherein the optical device includes:
an examination site;
a light source positioned to deliver light to the examination site;
a detector positioned to receive light transmitted from the examination site; and
an optical relay structure capable of delivering light from the light source substantially exclusively to a sensed volume of a sample positioned at the examination site.

15. The system of claim 14, wherein the optical relay structure also is capable of transmitting light to the detector substantially exclusively from a sensed volume of a sample positioned at the examination site.

16. The system of claim 1 further comprising a light source and a detector, wherein the optical device includes a fused-silica fiber optic cable that directs light from the light source toward the sample holder or from the sample holder toward the detector.

17. The system of claim 1, the optical device having an optical axis, wherein the optical device includes a confocal optics element that at least partially defines the extent of the sensed volume along the optical axis.

18. The system of claim 1, wherein the sample holder includes a reference fiducial disposed on the sample holder to provide information that facilitates the luminescence assay.

19. The system of claim 1, wherein the sample holder also is configured to reduce the formation and trapping of bubbles as the sample well is filled with a fluid sample.

20. The microplate of claim 19, wherein the sample well is configured to reduce the formation and trapping of bubbles through the choice of sample well coating.

21. The microplate of claim 19, wherein the sample well is configured to reduce the formation and trapping of bubbles through the geometry of the sample well.

22. The system of claim 1, where the maximum volume capacity of the sample holder is no greater than about 55 µL.

23. A system for detecting light transmitted from a sensed volume, the system comprising:
an optical device capable of detecting light substantially exclusively from a sensed volume; and
a sample holder configured to support a sample so that the shape of the sample substantially conforms to a conical portion of the sensed volume;
wherein the optical device has an optical axis; and
wherein the optical device includes a confocal optics element that at least partially defines the extent of the sensed volume along the optical axis.

24. The system of claim 23, wherein the sample holder has a frusto-conical shape.

25. The system of claim 23, further comprising at least a second sample holder, wherein the sample holders are disposed as wells in a microplate.

26. The system of claim 25, wherein the number of wells in the microplate is selected from the group consisting of 96, 384, and 1536.

27. The system of claim 25, wherein the wells are organized in a density of at least about 1 well per 81 $mm^2$.

28. The system of claim 23, wherein the sensed volume has a waist.

29. The system of claim 23, wherein the sensed volume has an hourglass shape, and wherein the sample holder has a conical shape configured to conform to substantially one-half of the hourglass shape.

30. The system of claim 23, wherein the sensed volume has an hourglass shape, and wherein the sample holder has a frusto-conical shape configured to conform to substantially one-half of the hourglass shape.

31. The system of claim 30, wherein the conical portion of the frusto-conical shape is characterized by a cone angle of at least about 8°.

32. The system of claim 30, wherein the conical portion of the frusto-conical sample holder is characterized by a cone angle of about 25°.

33. The system of claim 30, the sample holder having a top and a bottom, wherein the diameter of the bottom of the sample holder is about 1.5 millimeters.

34. The system of claim 23, wherein the sensed volume has an hourglass shape, and wherein the sample holder has a cylindrical shape configured to correspond to substantially all of the hourglass shape.

35. The system of claim 23, wherein the optical device includes:
an examination site;
a light source positioned to deliver light to the examination site;
a detector positioned to receive light transmitted from the examination site; and
an optical relay structure capable of transmitting light substantially exclusively from a sensed volume of a sample positioned at the examination site to the detector.

36. The system of claim 23, wherein the optical device includes:
an examination site;
a light source positioned to deliver light to the examination site;
a detector positioned to receive light transmitted from the examination site; and
an optical relay structure capable of delivering light from the light source substantially exclusively to a sensed volume of a sample positioned at the examination site.

37. The system of claim 36, wherein the optical relay structure also is capable of transmitting light to the detector substantially exclusively from a sensed volume of a sample positioned at the examination site.

38. The system of claim 36, further comprising a light source and a detector, wherein the optical device includes a fused-silica fiber optic cable that directs light from the light source toward the sample holder or from the sample holder toward the detector.

39. The system of claim 23, wherein the sample holder includes a reference fiducial disposed on the sample holder to provide information that facilitates the luminescence assay.

40. The system of claim 23, wherein the sample holder also is configured to reduce the formation and trapping of bubbles as the sample well is filled with a fluid sample.

41. The microplate of claim 40, wherein the sample well is configured to reduce the formation and trapping of bubbles through the choice of sample well coating.

42. The microplate of claim 40, wherein the sample well is configured to reduce the formation and trapping of bubbles through the geometry of the sample well.

43. The system of claim 23, where the maximum volume capacity of the sample holder is no greater than about 55 $\mu$L.

44. A system for detecting light transmitted from a sensed volume, the system comprising:
an optical device capable of detecting light substantially exclusively from a sensed volume; and
a sample holder configured to support a sample so that the shape of the sample substantially conforms to a conical portion of the sensed volume, wherein the sample holder also is configured through the choice of sample well coating to reduce the formation and trapping of bubbles as the sample well is filled with a fluid sample.

45. The system of claim 44, wherein the sample holder has a frusto-conical shape.

46. The system of claim 44, further comprising at least a second sample holder, wherein the sample holders are disposed as wells in a microplate.

47. The system of claim 46, wherein the number of wells in the microplate is selected from the group consisting of 96, 384, and 1536.

48. The system of claim 46, wherein the wells are organized in a density of at least about 1 well per 81 mm$^2$.

49. The system of claim 44, wherein the sensed volume has a waist.

50. The system of claim 44, wherein the sensed volume has an hourglass shape, and wherein the sample holder has a conical shape configured to conform to substantially one-half of the hourglass shape.

51. The system of claim 44, wherein the sensed volume has an hourglass shape, and wherein the sample holder has a frusto-conical shape configured to conform to substantially one-half of the hourglass shape.

52. The system of claim 51, wherein the conical portion of the frusto-conical shape is characterized by a cone angle of at least about 8°.

53. The system of claim 51, wherein the conical portion of the frusto-conical sample holder is characterized by a cone angle of about 25°.

54. The system of claim 51, the sample holder having a top and a bottom, wherein the diameter of the bottom of the sample holder is about 1.5 millimeters.

55. The system of claim 44, wherein the sensed volume has an hourglass shape, and wherein the sample holder has a cylindrical shape configured to correspond to substantially all of the hourglass shape.

56. The system of claim 44, wherein the optical device includes:
an examination site;
a light source positioned to deliver light to the examination site;
a detector positioned to receive light transmitted from the examination site; and
an optical relay structure capable of transmitting light substantially exclusively from a sensed volume of a sample positioned at the examination site to the detector.

57. The system of claim 44, wherein the optical device includes:
an examination site;
a light source positioned to deliver light to the examination site;
a detector positioned to receive light transmitted from the examination site; and
an optical relay structure capable of delivering light from the light source substantially exclusively to a sensed volume of a sample positioned at the examination site.

58. The system of claim 57, wherein the optical relay structure also is capable of transmitting light to the detector substantially exclusively from a sensed volume of a sample positioned at the examination site.

59. The system of claim 44 further comprising a light source and a detector, wherein the optical device includes a fused-silica fiber optic cable that directs light from the light source toward the sample holder or from the sample holder toward the detector.

60. The system of claim 44, wherein the sample holder includes a reference fiducial disposed on the sample holder to provide information that facilitates the luminescence assay.

61. The microplate of claim 44, wherein the sample well is configured to reduce the formation and trapping of bubbles through the geometry of the sample well.

62. The system of claim 44, where the maximum volume capacity of the sample holder is no greater than about 55 $\mu$L.

63. A system for detecting light transmitted from a sample, the system comprising:
an optical device configured to detect light originating substantially exclusively within a maximum cone; and
a sample holder for supporting the sample that includes a conical portion having a shape that substantially conforms to the shape of at least a portion of the maximum cone, wherein the cone angle of the conical portion is within 10° of the cone angle of the maximum cone.

64. The system of claim 63, the maximum cone having a cone angle $\theta$, wherein $\theta$ is given by the formula $\theta=2\arcsin(NA/n)$, where "NA" is the numerical aperture of the optical device, and "n" is the index of refraction of the medium adjacent the optical device.

65. The system of claim 64, wherein the numerical aperture lies in a range from about 0.07 to about 0.5.

66. The system of claim 65, wherein the index of refraction lies in a range from about 1.0 to about 1.25.

67. The system of claim 63, the maximum cone having a cone angle $\theta$, the optical device having an objective lens and a focal plane, wherein $\theta$ is the angle subtended at the focal plane by the objective lens.

68. The system of claim 63, the maximum cone having a cone angle $\theta$, the optical device having an optical axis, wherein $\theta$ is twice the angle made by a marginal ray relative to the optical axis.

69. The system of claim 63, the conical portion having a cone axis, wherein the sample holder also includes a planar portion having an orientation substantially perpendicular to the cone axis.

70. The system of claim 69, the planar portion characterized by a planar portion diameter, the optical device having a confocal aperture characterized by an aperture diameter, wherein the planar portion diameter is approximately equal to the aperture diameter.

71. The system of claim 63, wherein the maximum cone is characterized by a cone angle equal to or greater than about 8°.

72. A system for detecting light transmitted from a sample, the system comprising:
- an optical device configured to detect light originating substantially exclusively within a maximum cone; and
- a sample holder for supporting the sample that includes a conical portion having a shape that substantially conforms to the shape of at least a portion of the maximum cone;
- wherein the maximum cone has a cone angle $\theta$; and
- wherein $\theta$ is given by the formula $\theta=2\arcsin(NA/n)$, where "NA" is the numerical aperture of the optical device, and "n" is the index of refraction of the medium adjacent the optical device.

73. The system of claim 72, wherein the numerical aperture lies in a range from about 0.07 to about 0.5.

74. The system of claim 73, wherein the index of refraction lies in a range from about 1.0 to about 1.25.

75. The system of claim 72, the maximum cone having a cone angle $\theta$, the optical device having an objective lens and a focal plane, wherein $\theta$ is the angle subtended at the focal plane by the objective lens.

76. The system of claim 72, the maximum cone having a cone angle $\theta$, the optical device having an optical axis, wherein $\theta$ is twice the angle made by a marginal ray relative to the optical axis.

77. The system of claim 72, the conical portion having a cone axis, wherein the sample holder also includes a planar portion having an orientation substantially perpendicular to the cone axis.

78. The system of claim 77, the planar portion characterized by a planar portion diameter, the optical device having a confocal aperture characterized by an aperture diameter, wherein the planar portion diameter is approximately equal to the aperture diameter.

79. The system of claim 72, wherein the maximum cone is characterized by a cone angle equal to or greater than about 8°.

80. A system for detecting light transmitted from a sample, the system comprising:
- an optical device configured to detect light originating substantially exclusively within a maximum cone, where the optical device has a confocal aperture characterized by an aperture diameter; and
- a sample holder for supporting the sample that includes a conical portion and a planar portion, where the conical portion has a cone axis, and the planar portion is characterized by a planar portion diameter;
- wherein the conical portion has a shape that substantially conforms to the shape of at least a portion of the maximum cone;
- wherein the planar portion has an orientation substantially perpendicular to the cone axis; and
- wherein the planar portion diameter is approximately equal to the aperture diameter.

81. The system of claim 80, the maximum cone having a cone angle $\theta$, the optical device having an objective lens and a focal plane, wherein $\theta$ is the angle subtended at the focal plane by the objective lens.

82. The system of claim 80, the maximum cone having a cone angle $\theta$, the optical device having an optical axis, wherein $\theta$ is twice the angle made by a marginal ray relative to the optical axis.

83. The system of claim 80, wherein the maximum cone is characterized by a cone angle equal to or greater than about 8°.

* * * * *

UNITED STATES PATENT AND TRADEMARK OFFICE
CERTIFICATE OF CORRECTION

PATENT NO. : 6,488,892 B1
DATED : December 3, 2002
INVENTOR(S) : William G. Burton et al.

It is certified that error appears in the above-identified patent and that said Letters Patent is hereby corrected as shown below:

Title page,
Item [63], Related U.S. Application, delete "and" and insert -- which is -- therefor; delete "which is" and insert -- and -- therefor; and delete "which is" and insert -- and -- therefor.

Column 29,
Lines 50 and 53, delete "microplate" and insert -- system -- therefor.

Column 30,
Line 66, after "claim 36" delete ",".

Column 31,
Lines 11 and 14, delete "microplate" and insert -- system -- therefor.

Signed and Sealed this

Twenty-sixth Day of October, 2004

JON W. DUDAS
*Director of the United States Patent and Trademark Office*